(12) United States Patent
Rahmouni et al.

(10) Patent No.: US 8,927,014 B2
(45) Date of Patent: *Jan. 6, 2015

(54) MISUSE PREVENTATIVE, CONTROLLED RELEASE FORMULATION

(71) Applicants: Paladin Labs Inc., Montreal (CA); Paladin Labs (Barbados) Inc., Hastings, Christ Church (BB); Paladin Labs Europe Limited, Dublin (IE)

(72) Inventors: Miloud Rahmouni, Pierrefonds (CA); Sonia Gervais, Laval (CA); Vinayak Sant, Pittsburgh, PA (US); Damon Smith, Saint-Laurent (CA); Frederic Duffayet, Montreal (CA); Shams Rustom, Saint-Laurent (CA); Ali El-Jammal, Beaconsfield (CA); Jean-Michel Ndong, Repentigny (CA); Ali Bichara, Ste-Therese (CA)

(73) Assignees: Paladin Labs Inc., Montreal (CA); Paladin Labs (Barbados) Inc., Hastings (BB); Paladin Labs Europe Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/305,935

(22) Filed: Jun. 16, 2014

(65) Prior Publication Data

US 2014/0294955 A1    Oct. 2, 2014

Related U.S. Application Data

(63) Continuation of application No. 14/195,833, filed on Mar. 3, 2014, which is a continuation of application No. 13/919,499, filed on Jun. 17, 2013, now Pat. No. 8,685,447, which is a continuation of application No. 12/639,664, filed on Dec. 16, 2009, now Pat. No. 8,486,449.

(60) Provisional application No. 61/138,092, filed on Dec. 16, 2008.

(51) Int. Cl.
*A61K 9/20* (2006.01)
*A61K 9/28* (2006.01)

(52) U.S. Cl.
CPC ............... *A61K 9/2027* (2013.01); *A61K 9/28* (2013.01); *A61K 9/2086* (2013.01); *A61K 9/205* (2013.01); *A61K 9/2054* (2013.01)
USPC ........... 424/464; 424/465; 424/468; 424/469; 424/470

(58) Field of Classification Search
USPC ......................................................... 424/464
See application file for complete search history.

(56) References Cited

U.S. PATENT DOCUMENTS

| | | |
|---|---|---|
| 3,004,613 A | 10/1961 | Murphey et al. |
| 3,773,995 A | 11/1973 | Davies |
| 3,966,940 A | 6/1976 | Pachter et al. |
| 4,070,494 A | 1/1978 | Hoffmeister et al. |
| 4,820,522 A | 4/1989 | Radebaugh et al. |
| 4,968,509 A | 11/1990 | Radebaugh et al. |
| 5,004,613 A | 4/1991 | Radebaugh et al. |
| 5,133,974 A | 7/1992 | Paradissis et al. |
| 5,336,691 A | 8/1994 | Raffa et al. |
| 5,456,921 A | 10/1995 | Mateescu et al. |
| 5,478,577 A | 12/1995 | Sackler et al. |
| 5,591,452 A | 1/1997 | Miller et al. |
| 5,601,842 A | 2/1997 | Bartholomaeus |
| 5,603,956 A | 2/1997 | Mateescu et al. |
| 5,616,343 A | 4/1997 | Cartilier et al. |
| 5,672,360 A | 9/1997 | Sackler et al. |
| 5,681,583 A | 10/1997 | Conte et al. |
| 5,773,031 A | 6/1998 | Shah et al. |
| 6,103,261 A | 8/2000 | Chasin et al. |
| 6,156,342 A | 12/2000 | Sriwongjanya et al. |
| 6,159,501 A | 12/2000 | Skinhoj |
| 6,194,000 B1 | 2/2001 | Smith et al. |
| 6,210,714 B1 | 4/2001 | Oshlack et al. |
| 6,228,863 B1 | 5/2001 | Palermo et al. |
| 6,245,357 B1 | 6/2001 | Edgren et al. |
| 6,245,387 B1 | 6/2001 | Hayden |
| 6,254,887 B1 | 7/2001 | Miller et al. |
| 6,284,273 B1 | 9/2001 | Lenaerts et al. |
| 6,306,425 B1 | 10/2001 | Tice et al. |
| 6,309,668 B1 | 10/2001 | Bastin et al. |

(Continued)

FOREIGN PATENT DOCUMENTS

| | | | |
|---|---|---|---|
| CA | 2596965 A1 | 8/2006 | |
| CA | 2647360 A1 | 9/2007 | |

(Continued)

OTHER PUBLICATIONS

Amabile, C.M. et al. "Overview of oral modified-release opiod products for the management of chronic pain" *Ann. Pharmacother.* 40:1327-1335 (2006).

(Continued)

*Primary Examiner* — Hasan Ahmed
(74) *Attorney, Agent, or Firm* — Goodwin Procter LLP

(57) ABSTRACT

Disclosed is a misuse preventative, controlled release composition in the form of a multilayered oral dosage form. A first layer contains a plurality of controlled release microparticles having a pharmaceutically active agent (for example, an opioid analgesic) disposed therein. A second layer comprises a superabsorbent material. When crushed, either intentionally or accidentally, and exposed to an aqueous medium, the superabsorbent material creates a hard gel that traps the microparticles. The hard gel and microparticles provide controlled release of the pharmaceutically active agent.

24 Claims, 16 Drawing Sheets

(56) References Cited

U.S. PATENT DOCUMENTS

| | | |
|---|---|---|
| 6,326,027 B1 | 12/2001 | Miller et al. |
| 6,340,475 B2 | 1/2002 | Shell et al. |
| 6,372,255 B1 | 4/2002 | Saslawski et al. |
| 6,387,404 B2 | 5/2002 | Oshlack et al. |
| 6,399,096 B1 | 6/2002 | Miller et al. |
| 6,488,962 B1 | 12/2002 | Berner et al. |
| 6,607,748 B1 | 8/2003 | Lenaerts et al. |
| 6,635,280 B2 | 10/2003 | Shell et al. |
| 6,667,060 B1 | 12/2003 | Vandecruys et al. |
| 6,696,066 B2 | 2/2004 | Kaiko et al. |
| 6,696,088 B2 | 2/2004 | Oshlack et al. |
| 6,723,340 B2 | 4/2004 | Gusler et al. |
| 6,733,783 B2 | 5/2004 | Oshlack et al. |
| 6,761,895 B2 | 7/2004 | Sawada et al. |
| 6,968,551 B2 | 11/2005 | Hediger et al. |
| 7,041,320 B1 | 5/2006 | Nuwayser |
| RE39,221 E | 8/2006 | Raffa et al. |
| 7,083,807 B2 | 8/2006 | Fanara et al. |
| 7,141,250 B2 | 11/2006 | Oshlack et al. |
| 7,144,587 B2 | 12/2006 | Oshlack et al. |
| 7,157,103 B2 | 1/2007 | Sackler |
| 7,169,752 B2 | 1/2007 | Mickle et al. |
| 7,172,767 B2 | 2/2007 | Kaiko et al. |
| 7,201,920 B2 | 4/2007 | Kumar et al. |
| 7,374,781 B2 | 5/2008 | Zhang et al. |
| 7,776,314 B2 | 8/2010 | Bartholomaus et al. |
| 8,114,383 B2 | 2/2012 | Bartholomaus et al. |
| 8,309,060 B2 | 11/2012 | Bartholomaus et al. |
| 8,337,888 B2 | 12/2012 | Wright et al. |
| 8,409,616 B2 | 4/2013 | Kumar et al. |
| 8,445,018 B2 | 5/2013 | Habib et al. |
| 8,486,448 B2 | 7/2013 | Rahmouni et al. |
| 8,486,449 B2 | 7/2013 | Rahmouni et al. |
| 8,685,447 B2 | 4/2014 | Rahmouni et al. |
| 8,691,270 B2 | 4/2014 | Rahmouni et al. |
| 2002/0054911 A1 | 5/2002 | Oh |
| 2002/0090394 A1 | 7/2002 | Leonard et al. |
| 2002/0187192 A1 | 12/2002 | Joshi et al. |
| 2003/0004177 A1 | 1/2003 | Kao et al. |
| 2003/0031712 A1 | 2/2003 | Kaiko et al. |
| 2003/0044458 A1 | 3/2003 | Wright et al. |
| 2003/0049317 A1 | 3/2003 | Lindsay |
| 2003/0064122 A1 | 4/2003 | Goldberg et al. |
| 2003/0065002 A1 | 4/2003 | Caruso et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0073714 A1 | 4/2003 | Breder et al. |
| 2003/0091635 A1 | 5/2003 | Baichwal et al. |
| 2003/0092724 A1 | 5/2003 | Kao et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0143269 A1 | 7/2003 | Oshlack et al. |
| 2003/0191147 A1 | 10/2003 | Sherman et al. |
| 2004/0013726 A1 | 1/2004 | Lenaerts et al. |
| 2004/0024006 A1 | 2/2004 | Simon |
| 2004/0092542 A1 | 5/2004 | Oshlack et al. |
| 2004/0126428 A1 | 7/2004 | Hughes et al. |
| 2004/0131552 A1 | 7/2004 | Boehm |
| 2004/0131671 A1 | 7/2004 | Zhang et al. |
| 2004/0161382 A1 | 8/2004 | Yum et al. |
| 2004/0186121 A1 | 9/2004 | Oshlack et al. |
| 2004/0202716 A1 | 10/2004 | Chan et al. |
| 2004/0202717 A1 | 10/2004 | Mehta |
| 2004/0228802 A1 | 11/2004 | Chang et al. |
| 2004/0228924 A1 | 11/2004 | Oshlack et al. |
| 2005/0048115 A1 | 3/2005 | Mangena et al. |
| 2005/0063909 A1 | 3/2005 | Wright et al. |
| 2005/0095291 A1 | 5/2005 | Oshlack et al. |
| 2005/0112067 A1 | 5/2005 | Kumar et al. |
| 2005/0112195 A1 | 5/2005 | Cruz et al. |
| 2005/0158382 A1 | 7/2005 | Cruz et al. |
| 2005/0163856 A1 | 7/2005 | Maloney et al. |
| 2005/0176644 A1 | 8/2005 | Mickle et al. |
| 2005/0176645 A1 | 8/2005 | Mickle et al. |
| 2005/0191244 A1 | 9/2005 | Bartholomaus et al. |
| 2005/0192309 A1 | 9/2005 | Palermo et al. |
| 2005/0222135 A1 | 10/2005 | Buschmann et al. |
| 2005/0266070 A1 | 12/2005 | Mickle et al. |
| 2005/0276852 A1 | 12/2005 | Davis et al. |
| 2006/0002860 A1 | 1/2006 | Bartholomaus et al. |
| 2006/0009478 A1 | 1/2006 | Friedmann et al. |
| 2006/0034872 A1 | 2/2006 | Woolf |
| 2006/0058331 A1 | 3/2006 | Galer et al. |
| 2006/0073102 A1 | 4/2006 | Huaihung et al. |
| 2006/0104909 A1 | 5/2006 | Vaghefi et al. |
| 2006/0110327 A1 | 5/2006 | Emigh et al. |
| 2006/0157491 A1 | 7/2006 | Whittle et al. |
| 2006/0165602 A1 | 7/2006 | Galer et al. |
| 2006/0172006 A1 | 8/2006 | Lenaerts et al. |
| 2006/0177380 A1 | 8/2006 | Emigh et al. |
| 2006/0240107 A1 | 10/2006 | Lenaerts et al. |
| 2006/0257473 A1 | 11/2006 | Puranajoti |
| 2007/0003618 A1 | 1/2007 | Lenaerts et al. |
| 2007/0014732 A1 | 1/2007 | Sackler |
| 2007/0020188 A1 | 1/2007 | Sackler |
| 2007/0020339 A1 | 1/2007 | Bear |
| 2007/0048376 A1 | 3/2007 | Baichwal et al. |
| 2007/0060500 A1 | 3/2007 | Mickle et al. |
| 2007/0128269 A1 | 6/2007 | Gervais et al. |
| 2007/0166234 A1 | 7/2007 | Kumar et al. |
| 2007/0190142 A1 | 8/2007 | Breitenbach et al. |
| 2007/0202049 A1 | 8/2007 | Guimberteau et al. |
| 2007/0207089 A1 | 9/2007 | Abreu |
| 2007/0212414 A1 | 9/2007 | Baichwal et al. |
| 2007/0224129 A1 | 9/2007 | Guimberteau et al. |
| 2007/0231268 A1 | 10/2007 | Emigh et al. |
| 2007/0237816 A1 | 10/2007 | Finkelstein |
| 2007/0264326 A1 | 11/2007 | Guimberteau et al. |
| 2007/0264327 A1 | 11/2007 | Kumar et al. |
| 2007/0269505 A1 | 11/2007 | Flath et al. |
| 2007/0281018 A1 | 12/2007 | Qiu et al. |
| 2008/0031901 A1 | 2/2008 | Qiu et al. |
| 2008/0063725 A1 | 3/2008 | Guimberteau et al. |
| 2008/0152595 A1 | 6/2008 | Emigh et al. |
| 2008/0248113 A1 | 10/2008 | Bartholomaus et al. |
| 2008/0260844 A1 | 10/2008 | Soula et al. |
| 2009/0175937 A1 | 7/2009 | Rahmouni et al. |
| 2010/0239662 A1 | 9/2010 | Rahmouni et al. |

FOREIGN PATENT DOCUMENTS

| | | |
|---|---|---|
| EP | 0566709 A1 | 10/1993 |
| EP | 0914097 A2 | 5/1999 |
| EP | 1041987 A1 | 10/2000 |
| EP | 1389092 A1 | 2/2004 |
| EP | 1685839 A1 | 8/2006 |
| EP | 1695700 A1 | 8/2006 |
| JP | H03223211 A | 10/1991 |
| JP | 2007/254340 A | 10/2007 |
| WO | WO-99/32120 A1 | 7/1999 |
| WO | WO-01/45676 A2 | 6/2001 |
| WO | WO-01/85287 A1 | 11/2001 |
| WO | WO-02/092059 A1 | 11/2002 |
| WO | WO-02/092060 A1 | 11/2002 |
| WO | WO-02/094254 A2 | 11/2002 |
| WO | WO-03/013476 A1 | 2/2003 |
| WO | WO-03/013479 A1 | 2/2003 |
| WO | WO-03/013525 A1 | 2/2003 |
| WO | WO-03/013538 A1 | 2/2003 |
| WO | WO-03/026743 A2 | 4/2003 |
| WO | WO-03/039561 A1 | 5/2003 |
| WO | WO-03/094812 A1 | 11/2003 |
| WO | WO-2004/006904 A1 | 1/2004 |
| WO | WO-2004/026262 A2 | 4/2004 |
| WO | WO-2004/026283 A1 | 4/2004 |
| WO | WO-2004/041154 A2 | 5/2004 |
| WO | WO-2004/054542 A2 | 7/2004 |
| WO | WO-2004/054570 A1 | 7/2004 |
| WO | WO-2004/062614 A2 | 7/2004 |
| WO | WO-2004/091512 A2 | 10/2004 |
| WO | WO-2004/093801 A2 | 11/2004 |

(56) References Cited

FOREIGN PATENT DOCUMENTS

| WO | WO-2005/018616 A1 | 3/2005 |
| WO | WO-2005/032555 A2 | 4/2005 |
| WO | WO-2005/053587 A1 | 6/2005 |
| WO | WO-2005/123042 A1 | 12/2005 |
| WO | WO-2006/058249 A2 | 6/2006 |
| WO | WO-2006/089973 A2 | 8/2006 |
| WO | WO-2006/110642 A2 | 10/2006 |
| WO | WO-2007/013975 A2 | 2/2007 |
| WO | WO-2007/085024 A2 | 7/2007 |
| WO | WO-2008/011596 A2 | 1/2008 |
| WO | WO-2009/076764 A1 | 6/2009 |
| WO | WO-2010/069050 A1 | 6/2010 |

OTHER PUBLICATIONS

American Pain Society. Principles of analgesic use in the treatment of acute pain and cancer pain, 4th edition. APS 1-64 (1999).
Ballantyne, J.C. et al. "Opioid therapy for chronic pain" *N. Engl. J. Med.* 349:1943-1953 (2003).
Beaulieu, A.D. et al. "A randomized, double blind, 8-week crossover study of once-daily controlled-release tramadol versus immediate-release tramadol taken as needed for chronic noncancer pain" *Clinical Therapeutics* 29:49-60 (2007).
Food and Drug Administration "FDA Asks Purdue Pharma to Withdraw Palladone for Safety Reasons" (Jul. 13, 2005) (1 page).
Food and Drug Administration "Information for Healthcare Professionals: Hydromorphone Hydrochloride Extended-Release Capsules (marketed as Palladone)" FDA alert Jul. 2005 (2 pages).
Gabrielsson et al. (2002) "Multivariate methods in pharmaceutical applications," *Journal of Chemometrics*, vol. 16, pp. 141-160.
Houmes, R.J.M. et al. "Efficacy and safety of tramadol versus morphine for moderate and severe postoperative pain with special regard to respiratory depression" *Anaesthesia and Analgesia* 74:510-514 (1992).
International Search Report, International Application No. PCT/CA2009/001823, mailed on Mar. 17, 2010 (5 pages).
IPER and Written Opinion for International Application No. PCT/CA2009/001823, mailed on Mar. 17, 2010 (9 pages).
Lee, C.R. et al. "Tramadol. A preliminary review of its pharmacodynamic and pharmacokinetic properties, and therapeutic potential in acute and chronic pain states" *Drugs* 46:313-340 (1993).
Lubrizol Pharmaceutical Polymers for Controlled Release Tablets and Capsules; Pharmaceutical Bulletin 30; Edition: May 31, 2011 (7 pages).
National Institute of Drug Abuse (NIDA). Commonly Abused Drugs. Updated May 19, 2010. http://www.nida.nih.gov/DrugPages/DrugsofAbuse.html (5 pages).
Pain therapeutics. Oradure Technology (http://www.durect.com/wt/durect/pagename/oradur) (2 pages) (2010).
Parrott, T. "Using opioid analgesics to manage chronic non-cancer pain in primary care" *J. Am. Board Fam. Pract.* 12:293-306 (1999).
Purdue Pharma Press release. Perdue Pharma Provides Update on Development of New Abuse-Resistant Pain Medications. Jun. 18, 2002. http://www.pharma.com/pressroom/news/oxycontinnews/20020618.htm (3 pages).
Reder, R.F. "Opioid formulations: tailoring to the needs in chronic pain" *Eur. J. Pain* 5 (suppl. A):109-111 (2001).
Resnick, R.B. et al. *Annu. Rev. Pharmacol. Toxicol.* 20:463-474 (1980).
Roberts, M. et al. "Influence of ethanol on aspirin release from hypermellose matrices" *Pharmaceutics* 332:31-37 (2007).
Scott, L.J. et al. "Tramadol: a review of its use in postoperative pain" *Drugs* 60:139-176 (2000).
Spiller, H.A. et al. "Epidemiology of inhalant abuse reported to two regional poison centers" *Journal of Toxicology—Clinical Toxicology* 35:167-173 (1997).
Supplementary European Search Report for European Patent Application No. EP 08 861 707.1, dated Sep. 30, 2013 (7 pages).
Tiwari, S.B. et al. "Controlled release formulation of tramadol hydrochloride using hydrophilic and hydrophobic matrix system" *AAPS Pharm. Sci. Tech.* 4:1-6 (2003).
US Department of Health & Human Services. Prescription Drug Abuse. Jul. 26, 2006. http://www.hhs.gov/asl/testify/t060726b.html (5 pages).
Woolf, C.J. et al. "Use and abuse of opioid analgesics: Potential method to prevent and deter non-medical consumption of prescription opioids" *Current Opinion in Investigational Drugs* 5:61-66 (2004).
Wu, W.N. et al. "Metabolism of the analgesic drug ULTRAM (tramadol hydrochloride) in humans: API-MS and MS/Ms characterization of metabolites" *Xenobiotica* 31:411-425 (2002).
Wu, W.N. et al. "Metabolism of the analgesic drug, tramadol hydrochloride, in rat and dog" *Xenobiotica* 32:423-441 (2001).

MISUSE PREVENTATIVE, CONTROLLED RELEASE FORMULATION

RELATED APPLICATIONS

This application is a continuation of U.S. patent application Ser. No. 14/195,833, filed Mar. 3, 2014, which is a continuation of U.S. patent application Ser. No. 13/919,499, filed Jun. 17, 2013, now U.S. Pat. No. 8,685,447, which is a continuation of U.S. patent application Ser. No. 12/639,664, filed Dec. 16, 2009, now U.S. Pat. No. 8,486,449, which claims the benefit of and priority to U.S. Provisional Patent Application Ser. No. 61/138,092, filed Dec. 16, 2008, the entire contents of each of which are incorporated by reference herein.

FIELD OF THE INVENTION

The present invention relates generally to a controlled release formulation for the delivery of at least one pharmaceutically active agent, and more specifically, the invention relates to a misuse preventative, controlled release formulation, which maintains its controlled release properties for at least one pharmaceutically active agent even when bisected or crushed, and exposed to various media.

BACKGROUND OF THE INVENTION

Although significant developments have been made in the field of drug delivery, concerns remain for drugs (for example, opioid analgesics) that are subject to abuse. Furthermore, the number of legitimate patients misusing such drugs, either deliberately or accidentally, represents a serious medical problem. In particular, patient risk can be heightened when controlled release formulations are used because larger amounts of the pharmaceutically active agent are typically incorporated into these formulations to facilitate reduced dosing frequency. However, while controlled release formulations offer greater convenience and often an improved adverse event profile, serious problems can occur if the control release mechanism is compromised in any way, for example, by accidental chewing or grinding of, or other damage to the tablet, or co-ingestion with alcohol. Under these scenarios, immediate release of the pharmaceutically active agent followed by the rapid absorption of up to a total daily dose of the pharmaceutical agent can have potentially fatal consequences.

While a number of approaches have been tried to address the abuse and misuse of certain drugs, including, for example, the use of deterrent formulations, agonist/antagonist formulations, and prodrug formulations, the commercialization of these approaches has been limited to date.

Deterrent formulations are formulations that contain a noxious substance, such as, capsaicin, an emetic, or niacin. The objective is to prevent deliberate abuse by inflicting a painful or otherwise unpleasant reaction should the formulation be crushed or otherwise damaged prior to ingestion. For example, U.S. Patent Publication Nos. 2003/0068370, 2003/0068392, and 2007/0020188 describe incorporation of aversive agents (e.g., a bitter agent, an irritant, or an emetic agent) into a dosage containing an opioid analgesic. The aversive agents discourage an abuser from tampering with the dosage form and thereafter inhaling or injecting the tampered dosage. The potential risk of such additives to the legitimate user who accidentally damages the tablet is not addressed by such formulations.

Antagonist formulations contain inhibitors (antagonists) of the therapeutic drug. When the formulation is crushed, the inhibitors are intended to prohibit or reverse the action of the pharmaceutically active agent, thereby reducing or eliminating any benefit for non-medical use. For example, naloxone is combined with pentazocine (Talwin®, sold by Sanofi-Winthrop) to deter parenteral abuse of pentazocine. Naloxone is intended to block the binding of pentazocine to opioid receptors. Similarly, naloxone has been added to a buprenorphine-containing formulation (Temgesic®, sold by Reckitt & Colman). In addition, naltrexone, an opioid receptor antagonist, has been added to a morphine-containing formulation (Embeda®, sold by King Pharmaceuticals, Inc.). It is understood, however, that this approach, can expose legitimate patients to unnecessary drugs, and can potentially inhibit effective therapy because the inhibitors may be released during normal passage through the gastrointestinal tract. These formulations also assume that effective inhibition can be achieved (i.e., that the bioavailability, pharmacokinetics and relative affinities of the agonist and antagonist can be matched so as to elicit effective inhibition in the intended recipient). U.S. Pat. Nos. 3,773,955 and 3,966,940, for example, describe formulations containing combinations of opioid agonists and antagonists, in which the antagonist does not block the therapeutic effect when the mixture is administered orally but blocks analgesia, euphoria or physical dependence when administered parenterally in crushed form by an abuser.

Prodrug formulations rely on in vivo metabolic conversion of the prodrug into the active drug by enzymes found, for example, in the gastrointestinal tract. While these formulations may prevent euphoria via intravenous or nasal administration of the drug, they do not address the problems associated with potential intoxication (for example, alcohol intoxication) post oral administration.

Because of such limitations with existing technologies, there exists an ongoing need for misuse preventative, controlled release formulations that can reduce the risk of intentional abuse and accidental misuse of formulations containing a pharmaceutically active agent.

SUMMARY OF THE INVENTION

The invention is based, in part, upon the discovery that it is possible to create a drug delivery platform where the compositions are oral dosage forms that permit the controlled release of at least one pharmaceutically active agent disposed within the formulation even after being sectioned (for example, bisected) or crushed. The platform is particularly useful for the administration of pharmaceutically active agents that are capable of misuse (either deliberate or accidental but in either case causing harm), abuse and/or that have a narrow therapeutic index. Agents capable of harmful misuse or abuse, include, for example, analgesics (for example, opioid analgesics), hypnotic agents, anxiolytic agents, central nervous system (CNS), and respiratory stimulating agents. Examples of narrow therapeutic index drugs include theophylline, lithium carbonate, and digoxin.

In one aspect, the invention provides a solid composition (oral dosage form) for the oral administration of at least one pharmaceutically active agent. The composition comprises (a) a first layer comprising a first population of controlled release microparticles having at least one pharmaceutically active agent disposed therein; (b) a second layer comprising a pharmaceutically active agent disposed therein; and (c) a superabsorbent material disposed within the first layer, the second layer, or both the first layer and the second layer. In another aspect, the invention provides a solid composition (oral dosage form) for the oral administration of at least one pharmaceutically active agent. The composition comprises (a) a first layer comprising a superabsorbent material and a first population of controlled release microparticles having at least one pharmaceutically active agent disposed therein; and (b) a second layer comprising a pharmaceutically active agent disposed therein.

In each of the foregoing aspects, when the composition is exposed intact to an aqueous environment, the pharmaceutically active agent disposed in the second layer is initially released at a faster rate than the pharmaceutically active agent disposed in the first layer. At least one pharmaceutically active agent is released from the intact formulation over a prolonged period of time (for example, for at least 6 hours, at least 8 hours, at least 12 hours, at least 18 hours, or at least 24 hours). In certain embodiments, at least 50%, preferably 60%, more preferably 70%, and even more preferably 80% of at least one pharmaceutically active agent is prevented from being released substantially immediately (for example, within 30 minutes) from the intact formulation.

In addition, when the composition is crushed and exposed to an aqueous environment, the superabsorbent material swells to create a hard, rigid gel that traps the microparticles, which remain substantially intact. As a result, and in addition to the controlled release properties provided by the microparticles themselves, the hard gel depending upon its composition, may provide controlled release of at least one pharmaceutically active agent disposed therein. Depending upon the mode of abuse, the compositions of the invention create an unpleasant experience for the abuser, make it difficult to extract the pharmaceutically active agent, and/or prevent dose dumping. For example, when crushed and snorted up a nostril, the superabsorbent material produces a hard gel that creates an unpleasant experience. Furthermore, if crushed and exposed to an extraction media, the superabsorbant material can absorb all of the extraction media. The resulting gel can be difficult to push through the needle of a syringe. Furthermore, when crushed and administered, the microparticles, or a combination of the microparticles and the gel, maintain controlled release of the pharmaceutically active agent and reduce or eliminate the potential for dose dumping. In certain embodiments, at least 50%, preferably 60%, more preferably 70%, and even more preferably 80% of at least one pharmaceutically active agent is prevented from being released substantially immediately (for example, within 30 minutes) from the formulation. As a result, the compositions of the invention prevent dose dumping in water, alcohol (for example, ethanol), and other media of various pH even if the formulations have been broken or crushed.

The pharmaceutically active agent present in the first layer and the pharmaceutically active agent present in the second layer can be the same. Alternatively, they can be different so that a first pharmaceutically active agent is present in the microparticles in the first layer and a second, different pharmaceutically active agent is present in the second layer. Furthermore, the first layer can further comprise another pharmaceutically active agent, which can be in free form or present within microparticles. Furthermore, the pharmaceutically active agent disposed in the second layer optionally can be present in a second population of controlled release microparticles.

The composition is multilayered and can comprise two, three, four or more different layers. In one embodiment, the first layer is adjacent the second layer. As such, the two layers can form a bilayer composition. In another embodiment, the composition comprises a third layer, that can be adjacent the first layer, adjacent the second layer, or is disposed between the first layer and the second layer.

At least one pharmaceutically active agent present in the second layer is initially (for example, within the first 15 minutes or within the first 30 minutes after exposure to an aqueous environment) released at a faster rate than the pharmaceutically active agent in the first layer. This can be achieved via a number of approaches. For example, the pharmaceutically active agent in the first layer is disposed in controlled release microparticles whereas the pharmaceutically active agent in the second layer is not present within or otherwise associated with controlled release microparticles. Furthermore, the first layer can comprise a first controlled release matrix whereas the second layer can comprise an immediate release matrix. Alternatively, the first layer can comprise a first controlled release matrix whereas the second layer comprises a second, different controlled release matrix, wherein the first controlled release matrix has slower release kinetics than the second controlled release matrix. It is understand that a particular dosage form will vary depending upon the pharmaceutically active agent or agents to be delivered and the release profile desired for each pharmaceutically active agent.

A variety of superabsorbent materials can be used in the practice of the invention. The superabsorbent material can be polymeric, which can include, for example, polysaccharides, polysaccharide derivatives, and synthetic polymers. Exemplary polymers include, for example, a starch graft copolymer, a cross-linked carboxymethylcellulose derivative, a cross-linked hydroxypropyl distarch phosphate, a hydrolyzed starch-acrylonitrile graft copolymer and a neutralized starch-acrylic acid graft copolymer, polyacrylic acid, polyacrylamido methylpropane sulfonic acid, polyvinyl acetic acid, polyvinyl phosphonic acid, polyvinyl sulfonic acid, isobutylene-maleic anhydride copolymer, carboxymethyl cellulose, alginic acid, carrageenan, polyaspartic acid, polyglutamic acid, polyvinyl amine, polydiallyl dimethyl ammonium hydroxide, polyacrylamidopropyl trimethyl ammonium hydroxide, polyamino propanol vinyl ether, polyallylamine, chitosan, polylysine, polyglutamine, polycarbophil, polycarbophilic calcium, polymethacrylic acid, polyacrylic acid, and mixtures thereof. In a preferred embodiment, the superabsorbent material is polycarbophil.

The superabsorbent material can constitute from about 1% to about 70% (w/w) of the layer in which it is present (e.g., the first layer, the second layer, or both the first and second layers or the optional third layer) or from about 4% to about 50% (w/w) of the layer in which it is present (e.g., the first layer, the second layer, or both the first and second layers or the optional third layer).

As discussed above, the first layer, the second layer, or both the first and second layers may further comprise a controlled release agent. Exemplary controlled release agents include, for example, acetate succinate, a polyvinyl derivative, polyethylene oxide, polyacrylic acid, modified starch, cross-linked high amylose starch, hydroxypropyl starch, hydroxypropyl methylcellulose phthalate, cellulose, microcrystalline cellulose, carboxymethylethyl cellulose, cellulose acetate, methylcellulose, ethylcellulose, hydroxypropyl cellulose, hydroxypropylmethyl cellulose, cellulose phthalate, cellulose acetate, cellulose acetate phthalate, cellulose acetate propionate, cellulose acetate succinate, cellulose acetate butyrate, cellulose acetate trimellitate, poloxamer, povidone, alginic acid, sodium alginate, polyethylene glycol, polyethylene glycol alginate, gums (for example, xanthan gums), polymethacrylate, a copolymer of methacrylic acid and ethyl acrylate, a copolymer of polymethyl vinyl ether and malonic acid anhydride, a copolymer of polymethyl vinyl ether and malonic acid or the ethyl-, isopropyl-, n-butylesters thereof, zein, and mixtures of any of the foregoing. Furthermore, the first layer, the second layer or both the first and second layers can further comprise a diluent, a lubricant, a glidant, or a mixture thereof. The second layer can further comprise a disintegrant. Disintegrants preferably are omitted from the first layer, because when intact compositions are exposed to an aqueous environment, disintegrants in the first layer may cause the first layer to break apart thereby permitting the superabsorbent material to prematurely swell and create a hard gel.

It is understood that the composition can further comprise a coating that encapsulates the first layer and the second layer. The coating can be a non-functional (aesthetic coating) or can be a functional coating. Exemplary functional coatings include a controlled released coating, (for example, a delayed release coating, such as an enteric coating), a moisture barrier, or a taste masking film. The controlled release coating can include a controlled release agent and/or can be a controlled release film coating.

The controlled release microparticles present in the first layer and optionally present in the second layer can comprise a controlled release agent (for example, cross-linked high amylose starch sold under the Tradename CONTRAMID® from Labopharm, Inc., Laval, Canada) that controls the release of the pharmaceutically active agent disposed therein and/or a controlled release coating or film. The microparticles have an average diameter in the range from about 1 μm to about 1000 μm. The microparticles, due to their small size and high radius of curvature, resist crushing if the formulation is crushed, for example, with a conventional pill crusher or between spoons or in a pestle and mortar. In one embodiment, the microparticles have an average diameter in the range from about of 200 μm to about 900 μm, or from about 300 μm to about 800 μm. The microparticles under certain circumstances have an average diameter of about 700 μm. In another embodiment, the controlled release microparticles have an average diameter in the range of from about 1 μm to about 400 μm, from about 5 μm to about 300 μm, or from about 10 μm to about 200 μm. The microparticles can have an average diameter of about 100 μm. The controlled release microparticles included in the first layer and optionally in the second layer can be coated with one or more controlled release films.

The compositions of the invention have certain properties. For example, in certain embodiments, when the composition is crushed and exposed to 900 mL of water in a U.S.P. Type I Apparatus with stirring at 100 rpm for 30 minutes at 37° C., less than about 50% by weight or optionally less than about 25% by weight of the pharmaceutically active agent originally present in the composition before it was crushed broken is released into the water. Alternatively or in addition, when the composition is crushed and exposed to 900 mL of an aqueous solution containing 60% (v/v) ethanol in a U.S.P. Type 1 Apparatus with stirring at 100 rpm for 30 minutes at 37° C., less than about 50% by weight or optionally less than about 25% by weight of the pharmaceutically active agent originally present in the composition before it was broken is released into the aqueous solution.

It is understood that the oral dosage forms of the invention can be in the form of a capsule, caplet, pill, or a compressed tablet.

In another aspect, the invention provides a method of providing controlled release of a pharmaceutically active agent to a mammal, for example, a human. The method comprises orally administering to an individual in need of the pharmaceutically active agent one or more of the controlled release compositions described herein.

BRIEF DESCRIPTION OF THE DRAWINGS

The foregoing and other objects, features and advantages of the invention will become apparent from the following description of preferred embodiments, as illustrated in the accompanying drawings. Like referenced elements identify common features in the corresponding drawings. The drawings are not necessarily to scale, with emphasis instead being placed on illustrating the principles of the present invention, in which:

In FIGS. 1A and 1B, the compositions are uncoated bilayers; in FIGS. 1C and 1D, the compositions are coated bilayers. In FIGS. 1A and 1C, controlled release microparticles containing a pharmaceutically active agent are disposed within a first layer (FIGS. 1A and 1C), and a pharmaceutically active agent, which can be the same or different, is disposed within a second layer of the bilayer composition. In FIGS. 1B and 1D, the second layer of the bilayer compositions also comprise microparticles containing a pharmaceutically active agent, which can be the same as or different to the pharmaceutically active agent in the microparticles disposed within the first layer.

In FIG. 2A, controlled release microparticles containing a pharmaceutically active agent are disposed within the first layer, and in FIG. 2B the controlled release microparticles are present within both the first layer and the second layer.

FIG. 3A shows the release profile of oxycodone HCl in potassium phosphate buffer at pH 6.8 for 12 hours (-Δ-), 0.1M hydrochloric acid at pH 1.2 for 12 hours (-●-), 0.1M hydrochloric acid at pH 1.2 for 1 hour followed by potassium phosphate buffer pH 6.8 for 11 hours (-■-), and 40% ethanol (-▼-). FIG. 3B shows the release profile of acetaminophen in potassium phosphate buffer at pH 6.8 for 12 hours (-Δ-), 0.1M hydrochloric acid at pH 1.2 for 12 hours (-●-), 0.1M hydrochloric acid at pH 1.2 for 1 hour followed by potassium phosphate buffer at pH 6.8 for 11 hours (-■-), and 40% ethanol (-▼-).

FIG. 6A shows the release profile of oxycodone HCl in acidified potassium phosphate aqueous solution at pH 3.0 (-□-), potassium phosphate buffer at pH 6.8 (-▲-), basified potassium phosphate aqueous solution at pH 10.0 (-◇-), water (-574-), 20% ethanol (-▽-), and 40% ethanol (-◆-). FIG. 6B shows the release profile of acetaminophen in acidified potassium phosphate aqueous solution at pH 3.0 (-□-), potassium phosphate buffer pH 6.8 (-▲-), basified potassium phosphate aqueous solution at pH 10.0 (-◇-), and water (-●-).

FIG. 7A shows the release profile of oxycodone HCl in 0.1M hydrochloric acid at pH 1.2 for 12 hours (-●-), potassium phosphate buffer pH 6.8 for 12 hours (-Δ-), and 0.1M hydrochloric acid at pH 1.2 for 1 hour followed by potassium phosphate buffer pH 6.8 for 11 hours (-■-). FIG. 7B shows the release profile of acetaminophen in 0.1M hydrochloric acid at pH 1.2 for 12 hours (-●-), potassium phosphate buffer pH 6.8 for 12 hours (-Δ-), and 0.1M hydrochloric acid at pH 1.2 for 1 hour followed by potassium phosphate buffer pH 6.8 for 11 hours (-■-).

FIG. 8A shows the release profile of oxycodone HCl in potassium phosphate buffer pH 6.8 (-Δ-), and 0.1M hydrochloric acid at pH 1.2 (-●-). FIG. 8B shows the release profile of acetaminophen in potassium phosphate buffer pH 6.8 (-Δ-), and 0.1M hydrochloric acid at pH 1.2 (-●-).

FIG. 10A shows the release profile of oxycodone HCl in potassium phosphate buffer pH 6.8 (-●-). FIG. 10B shows the release profile of acetaminophen in potassium phosphate buffer pH 6.8 (-●-).

FIG. 11A shows the release profile of oxycodone HCl in potassium phosphate buffer pH 6.8 (-●-), and FIG. 11B shows the release profile of acetaminophen in potassium phosphate buffer pH 6.8 (-●-).

FIG. 15A shows the release profiles of oxycodone HCl in whole tablets in phosphate buffer pH 6.8 (-■-), whole tablets in 40% ethanol (-◆-), bisected tablets in phosphate buffer pH 6.8 (-●-), and bisected tablets in 40% ethanol (-Δ-). FIG. 15B shows the release profiles of acetaminophen in whole tablets in phosphate buffer pH 6.8 (-■-), whole tablets in 40% ethanol (-◆-), bisected tablets in phosphate buffer pH 6.8 (-●-), and bisected tablets in 40% ethanol (-Δ-).

DETAILED DESCRIPTION OF THE INVENTION

The invention is based, in part, upon the discovery that it is possible to produce a controlled release platform that renders pharmaceutical compositions less susceptible to intentional abuse and accidental misuse than other controlled release compositions, while being free from noxious additives, active ingredient antagonists, prodrugs and the like. The formulations maintain their controlled release properties when bisected (broken in half) as can occur when a patient or care-giver breaks a tablet in half to make the tablet easier to swallow. Even when crushed, the compositions of the invention prevent dose dumping because the microparticles contained within the composition remain substantially intact and retain their controlled release properties. The crushed formulations cannot easily be administered intravenously via a syringe because of hard gel formation, and if crushed and administered nasally, they swell causing an unpleasant sensation.

In one aspect, the invention provides a controlled release multilayer composition comprising: (a) a first layer comprising a first population of controlled release microparticles having a pharmaceutically active agent disposed therein; (b) a second layer comprising a pharmaceutically active agent disposed therein; and (c) a superabsorbent material (e.g., polycarbophil) disposed within the first layer, the second layer, or both the first layer and the second layer. In another aspect, the invention provides a controlled release multilayer composition comprising: (a) a first layer comprising a superabsorbent material (for example, polycarbophil) and a plurality of controlled release microparticles having at least one pharmaceutically active agent disposed therein. The second layer comprises a pharmaceutically active agent that can be the same as or different from the pharmaceutically active agent present in the microparticles of the first layer. In each aspect of the invention, the first and second layers can be encapsulated with either a non-functional coating or a functional coating. When the compositions are crushed, the microparticles remain substantially intact and control the release of the pharmaceutically active agent disposed therein and prevent dose dumping. As used herein, the term "dose dumping" is understood to mean an uncontrolled release of a pharmaceutically active agent where at least 80% of the pharmaceutically active agent in the formulation is released within 30 minutes (a specification that can be used to characterize a formulation as an immediate release formulation).

Figure 1:
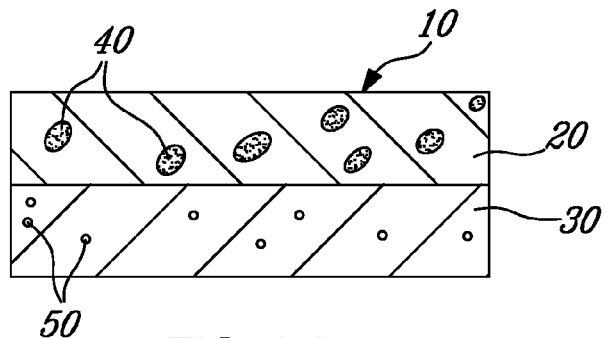
FIGS. 1A-1D show a schematic representation of exemplary misuse preventative, controlled release compositions.
Figure 1:
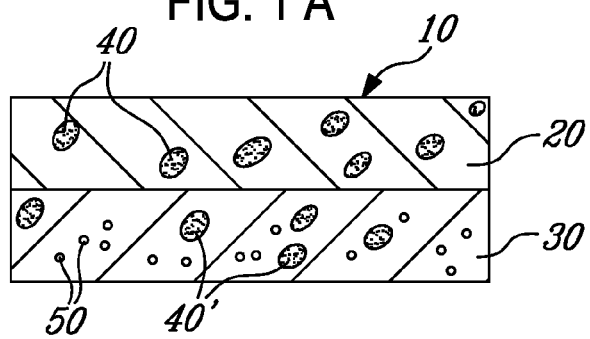
Figure 1:
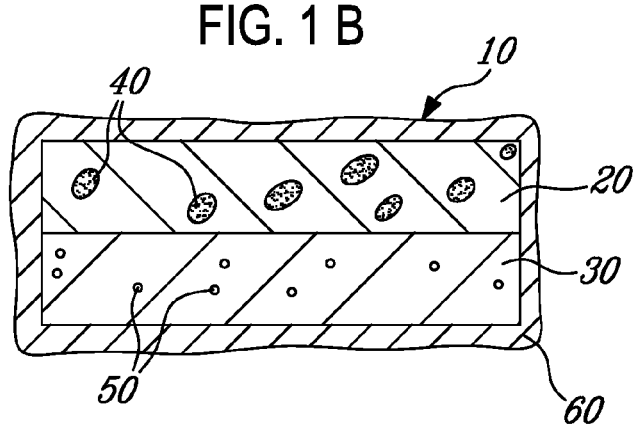
Figure 1:
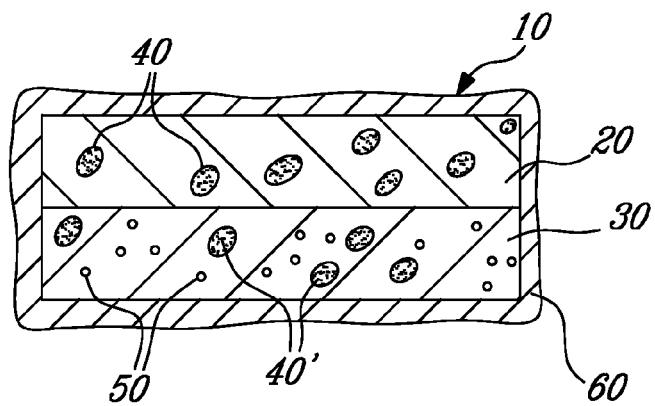
Figure 2:
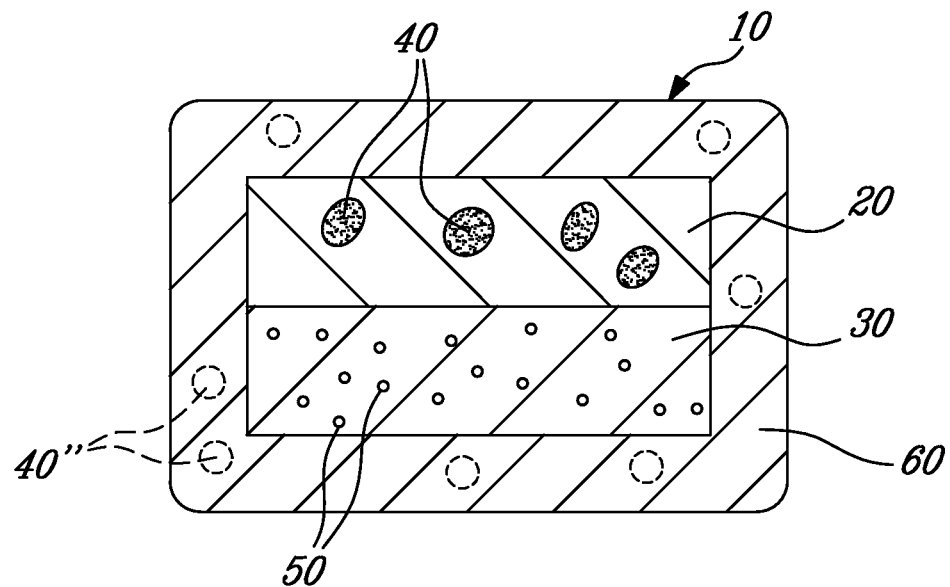
FIGS. 2A and 2B show a schematic representation of exemplary misuse preventative, controlled release formulations which are similar to those presented in FIGS. 1C and 1D, except the coatings are functional coatings, for example, a controlled release coating achievable by one or more of the following—a controlled release film, a controlled release agent, and controlled release microparticles.
Figure 2:
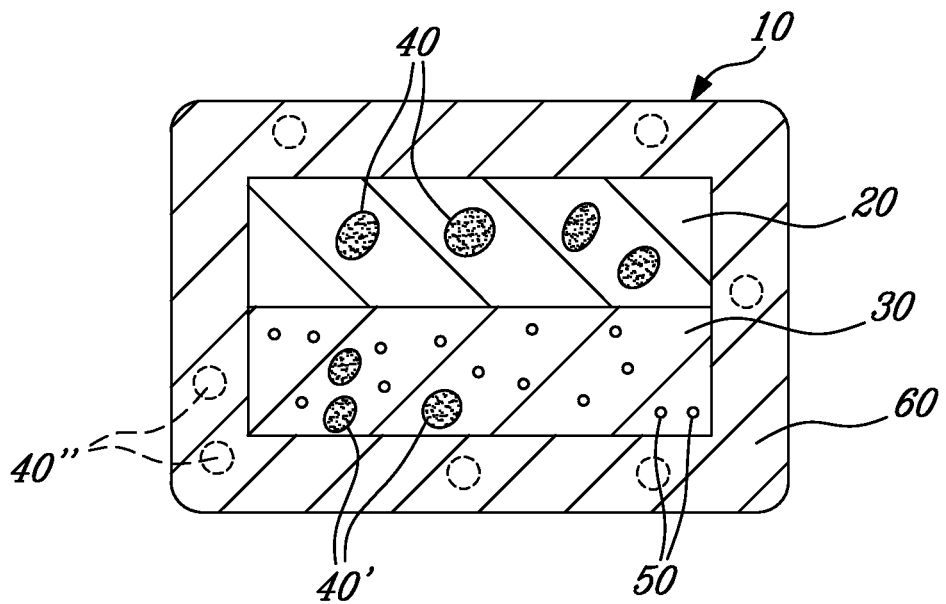

FIGS. 1A-1D, 2A, and 2B show certain embodiments of the oral dosage formulation of the invention. Each exemplary formulation contains a bilayer composition 10 having a first layer 20 and a second layer 30. In each formulation, the first layer contains a plurality of controlled release microparticles 40 that comprise a pharmaceutically active agent. The second layer of each formulation contains a second pharmaceutically active agent 50, which can be the same or different as the pharmaceutically active agent present in the microparticles in the first layer. Either the first layer, the second layer, or both the first and second layers can contain a superabsorbent material. In FIGS. 1B and 1D, the second layer also contains controlled release microparticles 40', which may be the same as or different from microparticles 40 disposed in the first layer 10. In the embodiments shown in FIGS. 1A and 1B, the bilayer is not coated; however, in the embodiments shown in FIGS. 1C and 1D, the bilayers are encapsulated in a coat, for example, a non-functional (aesthetic) coat. The embodiments depicted in FIGS. 2A and 2B are similar to those depicted in FIGS. 1C and 1D except coating 60 is a functional coating. As shown, the coating is a controlled release coating that is defined by a controlled release film, or is a coating containing a controlled release agent and/or controlled release microparticles 40", which can be the same as or different from the controlled release microparticles 40 disposed in first layer 20 or the optional controlled release microparticles 40' disposed in second layer 30. In each of the embodiments shown in FIGS. 1A-1D, 2A, and 2B, the microparticles control the release of the active ingredient irrespective of whether the tablet is intact or compromised (for example, by bisection or crushing). Furthermore, it is understood that the principles depicted in each of the figures can be present in multilayered dosage forms that contain more than two layers.

In one embodiment, first layer 20 is a controlled release layer in which the microparticles 40 enable a controlled release of the pharmaceutically active agent from the formulation over a prolonged period of time. Layer 20 can also comprise or define a controlled release matrix. The superabsorbent material, which can be disposed in layer 20, layer 30, or both layers 20 and 30 may also slow release of the pharmaceutically active agent, with minimal swelling upon contact with aqueous media. However, when the composition is crushed, a greater surface area of the superabsorbant material is exposed so that it swells rapidly to form a hard gel upon contact with an aqueous solvent.

In one embodiment, second layer 30 is an immediate release layer which allows for rapid disintegration and release of the second pharmaceutically active agent 50. Agent 50 may be the same as or different from agent 40. The second layer can also contain microparticles 40', which would provide delayed release of the pharmaceutically active agent disposed therein relative to the release of agent 50. In another embodiment, composition 10 may have a coating 60 that contains microparticles 40".

Under normal use, the compressed multilayered composition 10 has a hardness in the range of, for example, from about 100 N to about 500 N, such that the superabsorbent material in first layer 20, second layer 30, or both first and second layers 20 and 30 is prevented from absorbing aqueous solvent. As a result, the composition, even when combined with an aqueous solvent maintains sufficient integrity so that the majority of the superabsorbent material is prevented from swelling and disrupting the integrity of the multilayered composition. Furthermore, the resulting hardness renders the composition difficult to crush. When combined with an aqueous solvent, the solvent gradually permeates into both first layer 20 and second layer 30, and the pharmaceutically active agent present in second layer 30 is initially released faster than the pharmaceutically active agent present in the microparticles in first layer 20. As used herein, the term "initially released" refers to the release of at least one pharmaceutically active agent within 15 minutes or within 30 minutes after the composition has been exposed to an aqueous solvent. However, when crushed and exposed to an aqueous solvent, the superabsorbent material swells to form a rigid gel that encapsulates the microparticles. It is understood that the microparticles are a primary mechanism for controlling the release of the pharmaceutically active agent disposed therein. However, the hard, rigid gel that forms around the microparticles, along with other ingredients of the composition, can also impart controlled release properties in addition to those provided by the microparticles.

It is contemplated that the compositions described herein can be used for the delivery of one or more (for example, two, three, four or more) pharmaceutically active agents. With respect to all the embodiments depicted in FIGS. 1A-1D, 2A, and 2B, it is understood, for example, that microparticles 40 in first layer 20 can contain the same pharmaceutically active agent as the pharmaceutically active agent 50 present in second layer 30. As a result, such a bilayer composition permits the creation of a desired release profile, for example, with a fast initial release from second layer 30 followed by a slower subsequent release from first layer 20. Alternatively, the pharmaceutically active agent present in the microparticles 40 in the first layer may be different from free pharmaceutically active agent 50 in the second layer. For example, the pharmaceutically active agent in microparticles 40 in the first layer can be oxycodone whereas free pharmaceutically active agent 50 in second layer 30 can be acetaminophen. Furthermore, it is understood that the same pharmaceutically active agent in the second layer (for example, acetaminophen) can also be present in the free form (i.e., not included in or associated with microparticles) in the first layer. Such an example is depicted in Examples 1 and 2, wherein the microparticles in the first layer contain oxycodone, and acetaminophen is present in free form in both the first layer and the second layer.

In addition, it is contemplated that in the bilayer depicted in FIGS. 1A-1D, 2A, and 2B, first layer 20 can contain or define a controlled release matrix, whereas second layer 30 can define an immediate release matrix. Alternatively, first layer 20 and second layer 30 can both contain or define two different controlled release matrices. Furthermore, the compositions can further contain a non-functional or aesthetic coating (see, FIGS. 1C and 1D) or a functional coating (see, FIGS. 2A and 2B). It is understood, however, that the compositions can vary depending upon what pharmaceutically active agent or agents are to be released and what release profiles are desired for each agent.

In the case of an intact composition, when exposed to an aqueous environment (for example, a solution containing at least 10% (v/v) water), the pharmaceutically active agent disposed in the second layer is initially released (for example, within 15 minutes or within 30 minutes after exposure to an aqueous solvent) at a faster rate than the pharmaceutically active agent disposed in the first layer. At least one pharmaceutically active agent is released from the intact formulation over a prolonged period of time (for example, for at least 6 hours, at least 8 hours, at least 12 hours, at least 18 hours, or at least 24 hours). In certain embodiments, at least 50%, preferably 60%, more preferably 70%, and even more preferably 80% of at least one pharmaceutically active agent is prevented from being released substantially immediately (for example, within 30 minutes) from the intact composition when exposed to an extraction medium, for example, water, aqueous solutions ranging in pH from 1.2 to 6.8, and different ethanolic media (for example, water containing 20% ethanol, 40% ethanol, 60% ethanol, or 80% ethanol and 100% ethanol).

When the oral dosage form of the invention is bisected, for example, axially bisected, as can happen when a patient breaks a tablet in half to make it easier to swallow, the first and/or second layers become compromised to expose more superabsorbent material. However, based on the hardness of the first layer, only a small amount of the superabsorbent material swells and the resulting portions of the bisected tablet maintain their integrity. As a result, the bisected portions of the compositions of the invention have a release profile of the pharmaceutically active agent substantially the same as the intact composition. These principles are demonstrated, for example, in Example 1 and FIGS. 3-5 where the superabsorbent material is disposed within the first layer. Furthermore, even when bisected, the formulations of the invention permit the release of the pharmaceutically active agent over at least 6 hours, at least 12 hours, at least 18 hours, or over at least 24 hours. In certain embodiments, at least 50%, preferably 60%, more preferably 70%, and even more preferably 80% of at least one pharmaceutically active agent is prevented from being released substantially immediately (for example, within 30 minutes) from the formulation when exposed to an extraction medium, for example, water, aqueous solutions ranging in pH from 1.2 to 6.8, and different ethanolic media (for example, water containing 20% ethanol, 40% ethanol, 60% ethanol, or 80% ethanol and 100% ethanol).

When the oral dosage form of the invention is crushed (for example, with a commercially available pill crusher to break formulation into at least 10 particles or more) and then exposed to an aqueous environment, the superabsorbent material swells rapidly (for example, within about 30 seconds) to create a hard gel that traps the microparticles. Based in part upon their small size (high radius of curvature), the microparticles resist the crushing process and remain substantially intact. The hard gel provides an unpleasant experience if the crushed composition is snorted up a nostril and gel formation occurs within the nostril. This process has the advantage that the nasal secretions needed for absorption of the active ingredient into the blood-stream are absorbed by the superabsorbent material preventing intoxication via this route. Similarly, if the composition is crushed and exposed to an aqueous environment to extract the pharmaceutically active agent, the superabsorbant material in the core can absorb the extraction medium leaving little or no extraction medium to administer. In addition, the hard gel that is formed during this process cannot be drawn or pushed though a syringe needle.

In the case of compositions that have a controlled release coating, the coatings may be compromised by crushing. However the microparticles still permit the controlled release of the pharmaceutically active agent and prevent the pharmaceutically active agent from being released substantially immediately from the formulation (i.e., the microparticles provide controlled release of the pharmaceutically active agent) and the gel forms to entrap the microparticles. For example, at least 50%, preferably 60%, more preferably 70%, and even more preferably 80% of at least one pharmaceutically active agent is prevented from being released substantially immediately (for example, within 30 minutes) from the formulation (see, FIG. 6A, which is discussed in Example 1). As a result, the compositions of the invention prevent dose dumping in water, 20% ethanol, 40% ethanol, and 60% ethanol even if the formulations have been broken or crushed.

In certain embodiments, the compositions of the invention, when crushed and exposed to 900 mL of water in a U.S.P. Type I Apparatus with stirring at 100 rpm for 30 minutes at 37° C., less than about 50%, less than about 45%, less than about 40%, less than about 35%, less than about 30%, less than about 25%, or less than about 20% by weight of at least one pharmaceutically active agent originally present in the formulation before it was crushed is released into the water. In certain other embodiments, when the formulation of the invention is crushed and exposed to 900 mL of an aqueous solution containing 60% (v/v) ethanol in a U.S.P. Type I Apparatus with stirring at 100 rpm for 30 minutes at 37° C., less than about 50%, less than about 45%, less than about 40%, less than about 35%, less than about 30%, less than about 25%, or less than about 20% by weight of at least one pharmaceutically active agent originally present in the formulation before it was broken is released into the aqueous solution.

Each of the components of the formulation of the invention are discussed in the following sections.

A. Considerations for a Multilayer Component

It is understood that the multilayer can include two, three, four or more different layers. In one embodiment, the multilayer is a bilayer, where the first layer and the second layer are adjacent one another. In another embodiment, the compositions can comprise a third layer, which can be located adjacent the first layer, adjacent the second layer, or disposed between the first and second layers.

The first layer comprises a first population of controlled release microparticles having at least one pharmaceutically active agent disposed therein. The second layer comprises a pharmaceutically active agent disposed therein, which can be the same as or different from the pharmaceutically active agent in the microparticles disposed in the first layer. The first layer, the second layer, both the first and second layers, or an optional third layer can comprise a superabsorbent material. The pharmaceutically active agent disposed in the second layer is initially released at a faster rate than the pharmaceutically active agent disposed within the microparticles in the first layer. This can be achieved in a number of different ways, which include having at least one pharmaceutically active agent in the microparticles in the first layer but not the second layer. In addition, the first layer can comprise a controlled release agent or define a controlled release matrix whereas the second layer can define an immediate release matrix. Alternatively, the first layer and the second layers can both comprise a controlled release agent or define a controlled release matrix, but the compositions of each can be chosen so that pharmaceutically active agents are initially released from the second layer at a faster rate than from the first layer.

The term "superabsorbent material," as used herein is understood to mean any material that absorbs solvent, for example, 1 gram of material absorbs at least 30 mL, more preferably 50 mL of solvent, which, upon absorption of the solvent, swells to produce a hydrated gel (hydrogel). In general, useful superabsorbent materials, when exposed to an aqueous medium (for example, water), absorb in excess of 10-15 times, such as at least greater than 30 times, more preferably 50 times, of water based on its own weight. In certain embodiments, the superabsorbent material is a polymer.

Superabsorbent materials can be manufactured from polysaccharide derivatives or cross-linked polyelectrolytes. Polysaccharide superabsorbents include, but are not limited to, a starch graft copolymer, a crosslinked carboxymethylcellulose derivative, a hydrolyzed starch-acrylonitrile graft copolymer and a neutralized starch-acrylic acid graft copolymer. Cross-linked polyelectrolytes can contain functional groups such as carboxyl, sulfonate, sulphate, sulfite, phosphate, amine, imine, amide, quaternary ammonium or a mixture thereof. Examples of polyelectrolyte polymers include, but are not limited to, salts or partial salts of polyacrylic acid, polyacrylamido methylpropane sulfonic acid, polyvinyl acetic acid, polyvinyl phosphonic acid, polyvinyl sulfonic acid, an isobutylene-maleic anhydride copolymer, carboxymethyl cellulose, alginic acid, carrageenan, polyaspartic acid, polyglutamic acid, polyvinyl amine, polydiallyl dimethyl ammonium hydroxide, polyacrylamidopropyl trimethyl ammonium hydroxide, polyamino propanol vinyl ether, polyallylamine, chitosan, polylysine, polyglutamine and copolymers or mixtures thereof.

Exemplary superabsorbent materials can include a polymer selected from the group consisting of polycarbophil, polycarbophilic calcium, polymethacrylic acid, polyacrylic acid, and mixtures thereof. Polycarbophil is a superabsorbent polymer is capable of absorbing and retaining large quantities of water. Polycarbophil is a high molecular weight acrylic acid polymer cross-linked with divinyl glycol, and is sold under the tradename, NOVEON® AA-1, by Lubrizol Corporation OH, USA. It is understood that 1 gram of polycarbophil can absorb about 62 grams of water. Polycarbophil is stable and does not undergo hydrolysis or oxidation under normal conditions. Calcium salts of polycarbophil (polycarbophilic calcium) can be used and are available commercially under the tradename NOVEON® CA-1 or CA-2 from Lubrizol Corporation OH, USA. Other exemplary superabsorbent materials include Carbopol® polymers, which are acrylic acid polymers cross-linked with, for example, allyl ethers of pentaerythritol, for example, Carbopol® 71G (a carbomer homopolymer type A), Carbopol® 971P (a carbomer homopolymer type A), and Carbopol® 974 (a carbomer homopolymer type B), each of which is available from Lubrizol Corporation, OH, USA.

The superabsorbent material provides two functions. First, when the composition containing the superabsorbent material (for example, polycarbophil) is crushed and combined with solvent (for example, water) for parenteral injection, the superabsorbent material rapidly absorbs water, swells and forms a hard gel thus preventing injection. In addition, depending upon the amount of solvent added, all of the solvent may be absorbed leaving no residual solvent that can be administered. Second, if the composition is crushed and snorted into a nostril the superabsorbent material absorbs the liquid in the nostril causing the superabsorbent material to swell. Not only does the swelling cause discomfort but also prevents the drug disposed within the formulation from being rapidly released (for example, within less than 30 minutes).

In general, the proportion of the superabsorbent material in the first layer varies from about 1% (w/w) to about 70% (w/w) of the first layer, more preferably from about 2% (w/w) to about 50% (w/w) of the first layer. Furthermore, the superabsorbent material in the first layer varies from about 3% (w/w) to about 20% (w/w) of the final intact composition, more preferably from about 4% (w/w) to about 14% (w/w) of the final intact composition, more preferably from about 4% (w/w) to about 10% (w/w) of the final intact formulation.

Compositions of exemplary controlled release microparticles and methods for their manufacture are described in Section C below. In addition to the superabsorbent material and the microparticles, the first layer optionally further comprises or defines a controlled release matrix. In addition, depending up the circumstances, the second layer optionally further comprises or defines either an immediate release matrix or a controlled release matrix.

It is understood that materials that can be used to create a suitable controlled release matrix include, for example, acetyl succinate, a polyvinyl derivative (for example, polyvinyl alcohol, polyvinyl acetate, polyvinyl acetate phthalate, a copolymer of vinyl acetate and vinyl pyrrolidone, a copolymer of vinyl acetate and crotonic acid, polyvinylpyrollidone), polyethylene oxide, polyacrylic acid, polysaccharides (for example, modified starch, cross-linked high amylose starch, hydroxypropyl starch, hydroxypropyl methylcellulose phthalate, cellulose and cellulose derivatives (for example, microcrystalline cellulose, carboxymethylethyl cellulose, cellulose acetate, methylcellulose, ethyl cellulose, hydroxypropyl cellulose, hydroxypropylmethyl cellulose, cellulose phthalate, cellulose acetate, cellulose acetate phthalate, cellulose acetate propionate, cellulose acetate succinate, cellulose acetate butyrate, cellulose acetate trimellitate), poloxamer, povidone, alginic acid, sodium alginate, polyethylene glycol, polyethylene glycol alginate, gums (for example, xanthan gum), polymethacrylates (including, for example, a copolymer of methacrylic acid and methyl-methacrylate, and a copolymer of methacrylic acid and ethyl acrylate), a copolymer of polymethyl vinyl ether and malonic acid anhydride, a copolymer of polymethyl vinyl ether and malonic acid or the ethyl-, isopropyl-, n-butylesters thereof, zein, and mixtures of the foregoing.

It is understood that materials that can be used to create an immediate release matrix include, for example, microcrystalline cellulose, calcium phosphates (monobasic, dibasic and or tribasic), saccharides such as lactose, sucrose, dextrins, superdisintegrants such as croscarmalose sodium, sodium starch glycolate, and crospovidone.

In addition, the first layer and the second layer can comprise other excipients and manufacturing aids including, for example, one or more of, a diluent (for example, microcrystalline cellulose, lactose, dicalcium phosphate, sucrose), a lubricant (for example, sodium stearyl fumarate, magnesium stearate, calcium stearate, stearic acid, hydrogenated vegetable oils), a glidant (for example, colloidal silicon dioxide and talc), a dye (for example, iron oxide), and a filler (for example, lactose, pregelatinized starch, dextrin, maltose, calcium phosphates (monobasic, dibasic and/or tribasic), microcrystalline starch).

In addition, the second layer optionally includes a disintegrant to facilitate disintegration of the second layer. The disintegrants, however, typically are not included in the first layer so as to minimize the risk that the first layer disintegrates upon exposure to an aqueous media to expose the bulk of the superabsorbent material. It is preferred that the first layer remain intact when exposed to an aqueous environment. Useful disintegrants include, for example, crospovidone, sodium starch glycolate, sodium alginate, and croscarmellose.

B. Considerations for the Coat

It is understood that the multilayered composition as described in Section A can further comprise a coat (for example, a non-functional (aesthetic) coating as shown in FIGS. 1C and 1D or a functional coating (for example, a controlled release coat as shown in FIGS. 2A and 2B)). Under normal use, the coat still provides a rigid net-like structure that encapsulates the multilayer and can help minimize the swelling of the superabsorbent material.

Exemplary non-functional coatings include, for example, an aqueous based shellac dispersion MARCOAT 125® from Innovative Material Technologies, an aqueous dispersion of ethyl cellulose AQUACOAT® from FMC Biopolymers, methacrylic acid/ethyl acrylate copolymers KOLLICOAT® from BASF, hydroxypropylcellulose KLUCEL® from Aqualon, modified peas starch based aqueous film coating system LYCOAT® from Roquette, hydroxypropyl methylcellulose acetate succinate AQOAT® (HPMCAS) from Shin-Etsu, and OPADRY®, OPADRY TM®, OPADRY FX®, OPALUX®, OPAGLOS®, Ethocel® 10, 45, 100 cps (ethyl cellulose) all from Colorcon (PA, USA)

It is understood, however, that the coating can be a functional coating. In other words, the coating provides a function beyond aesthetics, which can include, for example, controlled release (such as delayed release) of an agent disposed within the composition, a moisture barrier, and a taste masking film.

The controlled release coatings can resist the release of drug as the pH of the extraction media varies (for example, when the formulations are combined with conventional carbonated beverages). Furthermore, the controlled release coatings can resist the release of drug in the presence of alcohol in the extraction media even at levels that exceed the alcohol content of alcoholic beverages.

In certain embodiments, the controlled release coating comprises a controlled release agent. Alternatively, or in addition, the coat is a controlled release film. Exemplary controlled release agents and film-coatings can be selected from the group consisting of acetyl succinate, a polyvinyl derivative (for example, polyvinyl alcohol, polyvinyl acetate, polyvinyl acetate phthalate, a copolymer of vinyl acetate and vinyl pyrrolidone, a copolymer of vinyl acetate and crotonic acid, polyvinylpyrollidone), polyethylene oxide, polyacrylic acid, polysaccharides (for example, modified starch, cross-linked high amylose starch, hydroxypropyl starch, hydroxypropyl methylcellulose phthalate, cellulose and cellulose derivatives (for example, microcrystalline cellulose, carboxymethylethyl cellulose, cellulose acetate, methylcellulose, ethylcellulose, hydroxypropyl cellulose, hydroxypropylmethyl cellulose, cellulose phthalate, cellulose acetate, cellulose acetate phthalate, cellulose acetate propionate, cellulose acetate succinate, cellulose acetate butyrate, cellulose acetate trimellitate)), poloxamer, povidone, alginic acid, sodium alginate, polyethylene glycol, polyethylene glycol alginate, gums (for example, xanthan gum), polymethacrylates (including, for example, a copolymer of methacrylic acid and methyl-methacrylate, and a copolymer of methacrylic acid and ethyl acrylate), a copolymer of methacrylic acid and ethyl acrylate, a copolymer of polymethyl vinyl ether and malonic acid anhydride, a copolymer of polymethyl vinyl ether and malonic acid or the ethyl-, isopropyl-, n-butylesters thereof, zein, and mixtures of the foregoing.

Further examples of controlled release film-coating polymers include, but are not limited to, methylcellulose, ethylcellulose (for example, Aquacoat® type from FMC Corp.), methylhydroxyethylcellulose, methylhydroxypropylcellulose (for example, Pharmacoat® type from Shin Etsu Corp.), ethylhydroxyethylcellulose, hydroxyethylcellulose, hydroxypropylcellulose, carboxymethylcellulose or methylcarboxymethylcellulose, acrylic polymers, polyvinylacetates, polyvinyl chlorides, polymethylmetacrylates or a terpolymer of vinylchloride, vinylalcohol and vinylacetate, hydroxypropylmethylcellulose phthalate (for example, HP type from Shin Etsu), hydroxypropylmethylcellulose acetate succinate (for example, Aqoat from Shin Etsu), cellulose acetate phthalate (for example, Aquacoat CPD from FMC Corp. or C-A-P NF from Eastman Chemical), polyvinyl acetate phthalate (for example, Sureteric from Colorcon), carboxymethylethylcellulose, and co-polymerized methacrylic acid/methacrylic acid methyl esters (for example, Eudragit from Degussa/Evonik Industries or Kollicoat from BASF or Acryl-Eze from Colorcon or Eastacryl from Eastman Chemical).

For example, Kollidon® SR (a powder consisting of polyvinyl acetate (8 parts, w/w) and polyvinyl pyrrolidone (2 parts, w/w)) can be used in combination with xanthan gum. Kollidon® SR is available from BASF, ON, Canada. Alternatively, the coat can be, for example, Eudragit® L30D 55, available from Degussa/Evonik Industries, NJ, USA. Furthermore, it is understood that, depending upon the release kinetics desired, the same controlled release agents and coatings can be disposed within or can coat the microparticles described below in Section C.

Exemplary moisture barriers include, for example, Opadry™ Moisture Barrier (AMB), high performance Opadry II (Colorcon, Pa., USA).

Exemplary taste masking films include, for example, Opadry™ (Colorcon, Pa., USA).

In addition, the coating can comprise one or more of a viscosity increasing agent (for example, xanthan gum, polyethylene oxide, polyvinylpyrollidone, cellulose and sucrose derivatives), a lubricant (for example, sodium stearyl fumarate, magnesium stearate and stearic acid), a glidant (for example, colloidal silicon dioxide and talc), and a dye (for example, iron oxide). In addition, the coating can comprise a plasticizer. Examples of plasticizers include, but are not limited to, cetanol, triacetin, citric acid esters, phthalic acid esters, dibutyl succinate, acetylated monoglyceride, acetyltributyl, acetyltributyl citrate, acetyltriethyl citrate, benzyl benzoate, calcium stearate, castor oil, chlorebutanol, colloidal silica dioxide, dibutyl phthalate, dibutyl sebacate, diethyl oxalate, diethyl malate, diethyl maleate, diethyl malonate, diethyl fumarate, diethyl phthalate, diethyl sebacate, diethyl succinate, dimethylphthalate, dioctyl phthalate, glycerin, glyceroltributyrate, glyceroltriacetate, glyceryl behanate, glyceryl monostearate, hydrogenated vegetable oil, lecithin, leucine, magnesium silicate, magnesium stearate, polyethylene glycol, propylene, glycol, polysorbate, silicone, stearic acid, talc, titanium dioxide, triacetin, tributyl citrate, triethyl citrate, zinc stearate, PEG (polyethylene glycol), and the like.

In addition, the coat can comprise controlled release microparticles containing a pharmaceutically active agent of interest. Compositions of exemplary controlled release microparticles and methods for their manufacture are described in the following section.

C. Considerations for the Controlled Release Microparticles

As shown in FIGS. 1A-1D, 2A, and 2B, the compositions of the invention comprise controlled release microparticles disposed within at least one layer of the multilayered composition (see, FIGS. 1A, 1C and 2A), two layers of the multilayered composition (see, FIGS. 1B, 1D and 2B), or within the controlled release coating (see, FIGS. 2A and 2B).

The controlled release microparticles contain a pharmaceutically active agent and facilitate the controlled release of the pharmaceutically active agent disposed therein. Depending upon the configuration chosen, the formulations can release the pharmaceutically active agent over a prolonged period of time, for example, at least 6 hours, at least 8 hours, at least 12 hours, at least 18 hours, or at least 24 hours.

Although the controlled release particles may take a variety of forms, they have a number of features in common, which include (i) they have controlled release properties and (ii) they are of a size that makes them hard to crush even when the formulations are crushed with a conventional pill crusher or the like. The microparticles may have a core and a coat, where either or both provide controlled release properties.

The core of the microparticles can comprise the pharmaceutically active agent and a variety of excipients, which include, for example, one or more of, a spheronizing agent, a plasticizer, and a controlled release agent. Exemplary spheronizing agents include, for example, microcrystalline cellulose, ethyl cellulose, low substituted hydroxypropylcellulose and dicalcium phosphate dihydrate. Microcrystalline cellulose is preferred and is available commercially under the tradename Avicel® PH101 from FMC BioPolymer, DE, USA. Microcrystalline cellulose forms a plastic and cohesive mass upon wetting, which is desirable for the successful production of spherical granules. Microcrystalline cellulose is considered to aid the spheronization process by absorbing water like a molecular sponge and helps in the binding and lubrication of the moistened powder mass during extrusion. During the spheronization process, moisture trapped in the microcrystalline cellulose microfibrils adds plasticity to the extrudate and helps convert short round extrudates obtained by extrusion into spherical pellets. Different grades of microcrystalline cellulose are commercially available, and a preferred grade suitable for extrusion-spheronization is Avicel® PH 101, because of its small particle size, low packing density and high water retentive capacity.

In addition, the core of the microparticles can contain a plasticizer. Exemplary plasticizers include, for example, Plasacryl® available from IMTech, PA, USA, and triethyl citrate available from Morflex, NC, USA.

In addition, the core of the microparticles optionally can contain a controlled release agent that controls the release of the pharmaceutically active agent. Exemplary controlled release agents can be selected from the group consisting of starch, starch derivatives, cellulose derivatives, xanthan gum, polyethylene glycol, polyvinyl acetate, polyvinyl alcohol, and mixtures thereof. In a preferred embodiment, the controlled release excipient includes a starch derivative that is a cross-linked high amylose starch, which provides the controlled release of the pharmaceutically active agent for at least 12 hours, for at least 18 hours, or for at least 24 hours. The cross-linked high amylose starch can be cross-linked with phosphorus oxychloride and/or can contain hydroxypropyl side chains. In certain embodiments, a suitable controlled release agent is commercially available from Labopharm, Inc., Laval, Canada, under the trademark CONTRAMID®. The synthesis of the CONTRAMID® excipient is described in U.S. Pat. No. 6,607,748.

The core of the microparticles containing a pharmaceutically active agent can be prepared by a variety of methods, including, for example, wet granulation and extrusion-spheronization. During wet granulation, microparticles are prepared using, for example, a fluid bed rotor granulator. The wet granulation process comprises, for example, (i) wetting the powder to form wet granules; (ii) exposing the wet granules to tumbling or spheronization, and (iii) drying the resulting product. Alternatively, the pellets can be produced by extrusion-spheronization, which has the advantage of being highly reproducible, easy to scale up, cost effective, and produces substantially perfect spherical microparticles. Extrusion-spheronization comprises, for example, (i) wetting the powder blend with an aqueous or organic solution generally containing a binder to form a wet homogeneous mass suitable for wet extrusion, (ii) extruding the wet mass to form cylindrical extrudates of uniform shape and size, and (iii) spheronizing the wet extrudates using a spheronizer, where, for example, a fast spinning disc, breaks the extrudates into smaller microparticles and rounds them to form spheres.

The cores of the microparticles can be coated with a controlled-release coating that is sufficiently flexible to be deformed under compression during tablet formation without undergoing fracture. Suitable controlled release agents are described in the previous section. In one embodiment, the controlled release coating comprises polymethacrylate (e.g., Eudragit® RS, available from Degussa/Evonik Industries, NJ, USA). Eudragit® RS30D grade, which is particularly useful, is an aqueous dispersion (30% w/w) of a polymeric mixture of ethyl acrylate, methyl methacrylate, and trimethylammonioethyl methacrylate at a ratio of 1:2:0.1 (w/w). The Eudragit® RS grade is designed to form water-insoluble film coats for sustained release formulations. The Eudragit® RS grade forms a highly flexible film coat with low permeability. Another useful coating material includes Eudagrit® RL30D 55, available from Degussa/Evonik Industries, NJ, USA. Another controlled release coating comprises ethyl cellulose sold under the tradename Surelease®. Another controlled release coating includes Kollicoat® SR, available from BASF Fine Chemicals. In one approach, the core of the microparticles is coated using a fluid bed coater equipped with a bottom spray.

The resulting particles, depending upon their composition and method of fabrication have an average diameter in the range of from about 1 µm to about 1000 µm. In certain embodiments, the microparticles have an average diameter of from about of 200 µm to about 900 µm, or from about 300 µm to about 800 µm. In certain embodiments, the resulting microparticles have an average diameter of about 700 µm. In certain other embodiments the microparticles have an average diameter of from about 1 µm to about 400 µm, from about 5 µm to about 300 µm, or from about 10 µm to about 200 µm. In certain embodiments, the resulting microparticles have an average diameter of about 100 µm.

D. Pharmaceutically Active Agents

It is understood that the compositions described herein can be used for the delivery of one or more pharmaceutically active agents. In certain embodiments, the controlled release microparticles can contain one or more pharmaceutically active agents. In addition, it is understood that the compositions of the invention can contain a number of different microparticles, with one population of microparticles containing one pharmaceutically active agent and another population of microparticles containing a second, different pharmaceutically active agent. Furthermore, it is understood that one or more of the pharmaceutically active agents can be present in microparticles whereas one or more other pharmaceutically active agents can be present in a free form within the composition (i.e., not disposed in or associated with a microparticle).

Many pharmaceutically active agents can benefit from being delivered using the formulations described herein. The Controlled Substances Act (CSA), Title II of the Comprehensive Drug Abuse Prevention and Control Act of 1970, places all substances that are regulated under existing Federal Law into one of five schedules based upon the substance's medicinal value, harmfulness, and potential for abuse or addiction. The formulations of the invention are preferably used to deliver those drugs classified as Schedule II, III, IV and V drugs. Similarly, although any drug in which there is a benefit in having controlled release of the drug can be incorporated into formulations of the invention, the formulations described herein are particularly useful in the delivery of, for example, CNS and respiratory stimulant agents, analgesics (for example, opioid analgesics), hypnotic agents, anxiolytic agents, and agents with a narrow therapeutic index. For purposes of this invention, pharmaceutically active agents are intended to encompass salts, esters, and the prodrugs of the pharmaceutically active agents.

Exemplary opioid analgesics include, for example, alfentanil, buprenorphine, butorphanol, carefentanil, codeine, dezocine, diacetylmorphine, dihydrocodeine, dihydromorphine, diprenorphine, etorphine, fentanyl, hydrocodone, hydromorphone, β-hydroxy-3-methylfentanyl, levo α-acetylmethadol, levorphanol, lofentanil, meperidine, methadone, morphine, nalbuphine, oxycodone, oxymorphone, pentazocine, pethidine, propoxyphene, remifentanil, sufentanil, tilidine, tramadol hydrochloride, or a mixture thereof.

In certain embodiments containing an opioid analgesic, the solid composition can further include acetaminophen as a second, different pharmaceutically active agent. Depending upon the desired properties of the composition, the acetaminophen can be included in the first layer, the second layer, or both the first and second layers. In certain formulations, the acetaminophen is not included within the microparticles as it is believed that, for certain users, the rapid release of acetaminophen may serve as an additional deterrent to crushing the compositions because acetaminophen is generally known to have toxicity at high concentrations.

Exemplary hypnotics include, for example, benzodiazepines and non-benzodiazepines. Exemplary benzodiazepines include, but are not limited to, alprazolam, diazepam, flurazepam, loprazolam, mexazolam, nitrazepam, and the like. Exemplary non-benzodiazepines include, but are not limited to, barbiturates (for example, butobarbitone, phenobarbitone, or amylobarbitone) chlormethiazole, eszopiclone, ramelteon, zaleplon, zopiclone, zolpidem, and the like.

Exemplary anxiolytic agents include, but are not limited to, amphetamine, buspirone, barbiturates, benzodiazepines (for example, alprazolan, bromazepam, brotizolam, camazepam, chlordiazepoxide, clobazam, clonazepam, desalkylflurazepam, diazepam, flunitrazepam, flurazepam, lorazepam, lometazepam, medazepam, metaclazepam, midazolam, nitrazepam, nordazepam, oxazepam, pentylenetetrazole, prazepam, temazepam, tetrazepam, and triazolam) and the like.

Exemplary CNS and respiratory stimulatory agents include, but are not limited to xanthines (for example, caffeine and theophylline), amphetamines (for example, amphetamine, benzphetamine hydrochloride, dextroamphetamine, dextroamphetamine sulfate, levamphetamine, levamphetamine hydrochloride, methamphetamine, and methamphetamine hydrochloride), and miscellaneous stimulants such as methylphenidate, methylphenidate hydrochloride, modafinil, pemoline, sibutramine, and sibutramine hydrochloride.

Pharmaceutically active agents with a narrow therapeutic index include, for example, amiodarone, amphotericin, cabamazepine, clozapine, digoxin, disopyramide, lithium carbonate, minoxidil, phenytoin, primidone, procainamide, quinidine, theophylline, valproic acid, and warfarin.

It will be appreciated that the amount of the pharmaceutically active agent present in the abuse-resistant formulation depends upon the therapeutic dose required in conventional tablets. In generally, each pharmaceutically active agent is present in an amount ranging from about 0.5 mg to about 900 mg by weight, from about 1 mg to about 700 mg by weight, from about 1 mg to about 600 mg by weight, from about 1 mg to about 500 mg, from about 1 mg to about 400 mg, from about 1 mg to about 300 mg, from about 1 mg to about 200 mg, and from about 10 mg to about 200 mg. It is understood, however, that the actual dosage will depend upon the particular pharmaceutically active ingredient and its proposed use.

It is understood that the intact compositions described herein can be produced using techniques known to those in the formulary arts. An exemplary protocol for producing controlled release tablets is described in Example 1. It is understood, however, that other approaches can be used to make formulations of the invention.

In certain embodiment, the formulations have a hardness in the range of from about 100 N to about 500 N, or from about 150 N to about 400N, or from about 200 N to about 400N, or from about 300 N to about 400 N. In certain embodiments, the formulations have a hardness from about 130 N to about 280 N, from about 130 N to about 210 N, from about 130 N to about 195 N, from about 150 N to about 250 N, from about 150 N to about 200 N, from about 150 N to about 180 N, from about 160N to about 195 N, from about 160 N to about 180 N, from about 180 N to about 230 N, from about 200 N to about 250 N, from about 200 N to about 260 N, from about 205 N to about 280 N, from about 210 to about 250 N, or from about 210 N to about 230 N.

In certain embodiments, for example, an oral dosage form containing oxycodone and acetaminophen can have a hardness within one or more of the ranges set forth above.

The composition, when made, can be used to administer a pharmaceutically active agent to a mammal, for example, a human, in need of the pharmaceutically active agent (for example, an opioid analgesic for pain management). It is understood that the exact dosage will vary depending on the symptoms, age, body weight, severity of the disease to be treated and can be optimized through routine experimentation known to those of skill in the art.

EXAMPLES

Practice of the invention will be more fully understood from the foregoing examples, which are presented herein for illustrative purposes only, and should not be construed as limiting the invention in any way.

Example 1

Exemplary Oxycodone HCl/Acetaminophen Tablet

This Example describes an exemplary misuse preventative tablet and how it can be made. The composition comprises a mixture of acetaminophen (650 mg) and oxycodone HCl (25 mg). Oxycodone is a drug used for the treatment of moderate to moderately severe pain, which is capable of being abused and for which over exposure via misuse can lead to harmful side effects. The tablet has a bilayer core with a non-functional (aesthetic) coating. In this Example, the superabsorbent material is disposed within the controlled release layer. The formulation of the tablet is set forth in Table 1, and the manufacture of each of the components for the formulation appear in the following sections of this Example.

TABLE 1

| Ingredients | Tablet Composition (Mg) | (%) |
|---|---|---|
| First layer (controlled release) | | |
| Oxycodone (as oxycodone microparticles) | 173.79 | 24.72 |
| COMPAP ® (which includes acetaminophen) | 433.33 | 61.64 |
| Carbopol 71 G | 42.02 | 5.98 |
| Xanthan gum 80 mesh | 42.02 | 5.98 |
| Colloidal silicon dioxide (Cab O sil) | 2.95 | 0.42 |
| Sodium stearyl fumarate (Pruv) | 8.86 | 1.26 |
| Total | 703.00 | 100.00 |
| Second layer (rapid release) | | |
| COMPAP ® (which includes acetaminophen) | 288.89 | 89.72 |
| Microcrystalline Cellulose PH102 | 19.77 | 6.14 |
| Croscaramellose sodium AcDiSol | 6.70 | 2.08 |
| Colloidal silicon dioxide (Cab O sil) | 1.68 | 0.52 |
| Sodium stearyl fumarate (Pruv) | 4.83 | 1.50 |
| FD&C Yellow #6 | 0.13 | 0.04 |
| Total | 322.00 | 100.00 |

Throughout the examples, COMPAP® (Mallinckrodt, Inc.) is a compressible composition that comprises an admixture of acetaminophen and pre-gelatinized starch, where the percentage of acetaminophen in the composition can vary slightly depending upon the batch of COMPAP®. To compensate for this variability, the amount of COMPAP® is varied in the blend of excipients to be compressed. Corresponding changes are made to the amount of microcrystaline cellulose in order to maintain tablet weight. In addition, the amount of oxycodone or other active ingredient contained within the microparticles can vary, so the amount of microparticles may be adjusted to keep the drug content constant.

A. Manufacture of Oxycodone Microparticles

The microparticles were produced by mixing the components set forth in Table 2 (except for the Eudragit NE 30D and Talc). The resulting mixture was subjected to extrusion and spheronization, and the resulting microparticles were coated with the Eudragit NE 30D and talc in a fluid bed coater equipped with a bottom spray. The core of the tablet was a bilayer. The oxycodone containing microparticles were incorporated in the slow release layer of the bilayer whereas the acetaminophen, as COMPAP® which was in free form and not incorporated into microparticles, was present in both the rapid release layer and the slow release layer.

TABLE 2

| Ingredients | Mg/tablet | % Composition |
|---|---|---|
| Oxycodone HCl | 20.0 | 11.51 |
| Cellulose microcrystalline (Avicel PH101) | 37.3 | 21.49 |
| Contramid ® excipient | 2.7 | 1.53 |
| Lactose monohydrate | 73.4 | 42.22 |
| Eudragit NE 30D | 20.0 | 11.51 |
| Talc | 20.0 | 11.51 |
| Colloidal silicon dioxide | 0.4 | 0.23 |
| Total | 173.8 | 100.00 |

B. Manufacture of the Bilayer

The composition of the first layer (controlled release layer) containing COMPAP® and the oxycodone containing microparticles, and the composition of the second layer containing COMPAP® (which includes acetaminophen) are shown in Table 1. The bilayer was prepared by mixing the components of each layer and then compressing the materials in a tablet press to form a tablet having a hardness of about 210 N.

C. Aesthetic Coat

The bilayer tablet was coated with an aesthetic coat using the Opaglos ingredients set forth in Table 3 using a pan coating machine to form the final coated tablet.

TABLE 3

| Ingredients | Mg/tablet | % tablet |
|---|---|---|
| Opaglos II Gray | 30.75 | 3.0 |
| Opaglos II Clear | 10.25 | 1.0 |

Figure 3A:
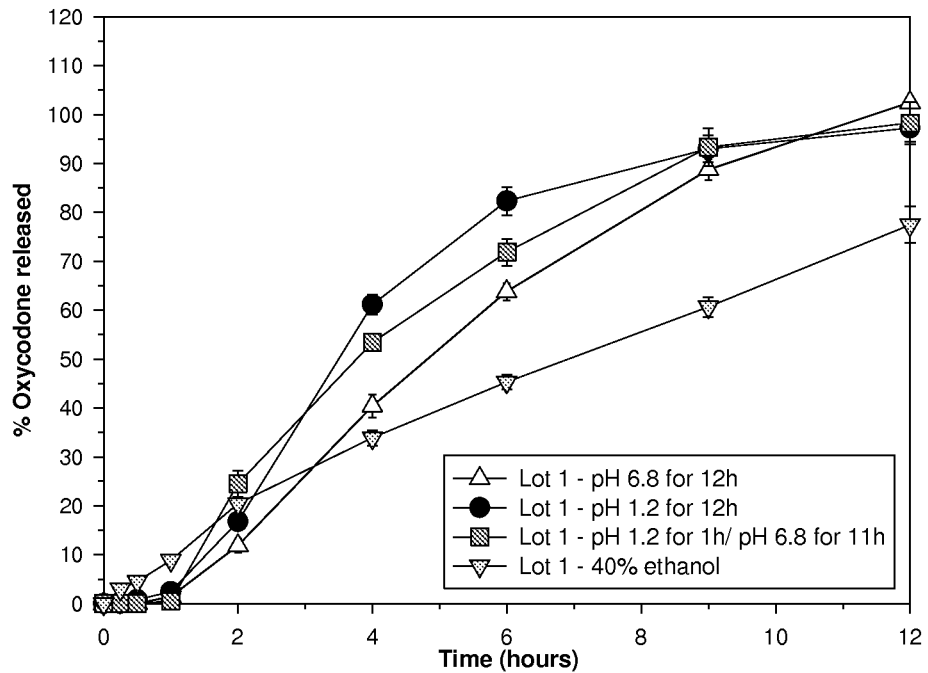
FIGS. 3A and 3B are graphs showing the in vitro dissolution profile of oxycodone HCl (FIG. 3A) and acetaminophen (FIG. 3B) from an intact, exemplary controlled release formulation of the invention in a U.S.P. Type III Apparatus.
Figure 3B:
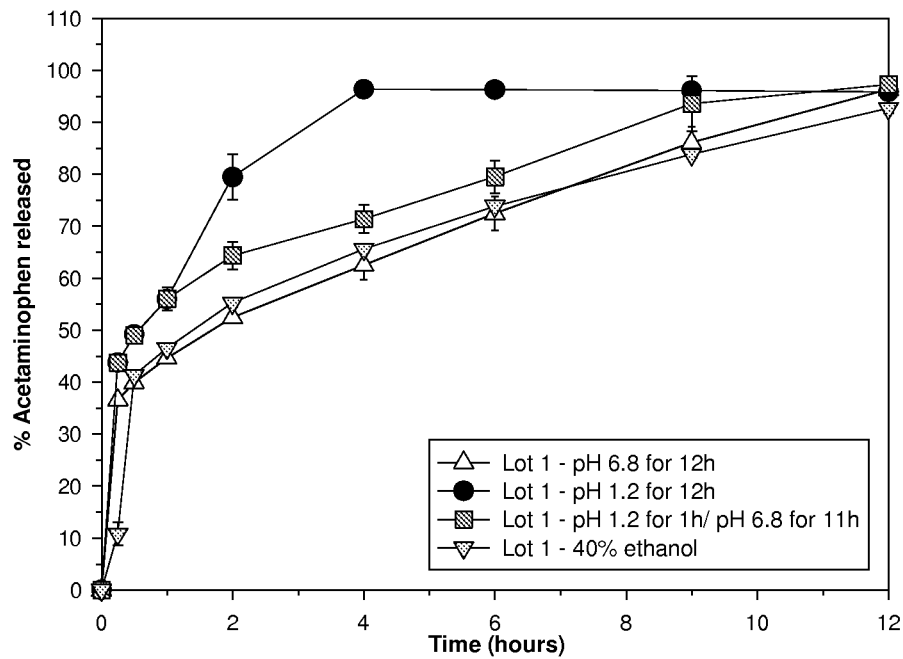

The in vitro release properties of the resulting tablets were measured in a U.S.P. Type III Apparatus in potassium phosphate buffer at pH 6.8 for 12 hours, 0.1M hydrochloric acid at pH 1.2 for 12 hours, 0.1M hydrochloric acid at pH 1.2 for 1 hour followed by potassium phosphate buffer at pH 6.8 for 11 hours, and in 40% ethanol. As shown in FIG. 3A, the release profiles for oxycodone were substantially the same across the pH range tested. In addition, as shown in FIG. 3B, the release properties for acetaminophen were substantially the same across the pH range tested.

Figure 4A:
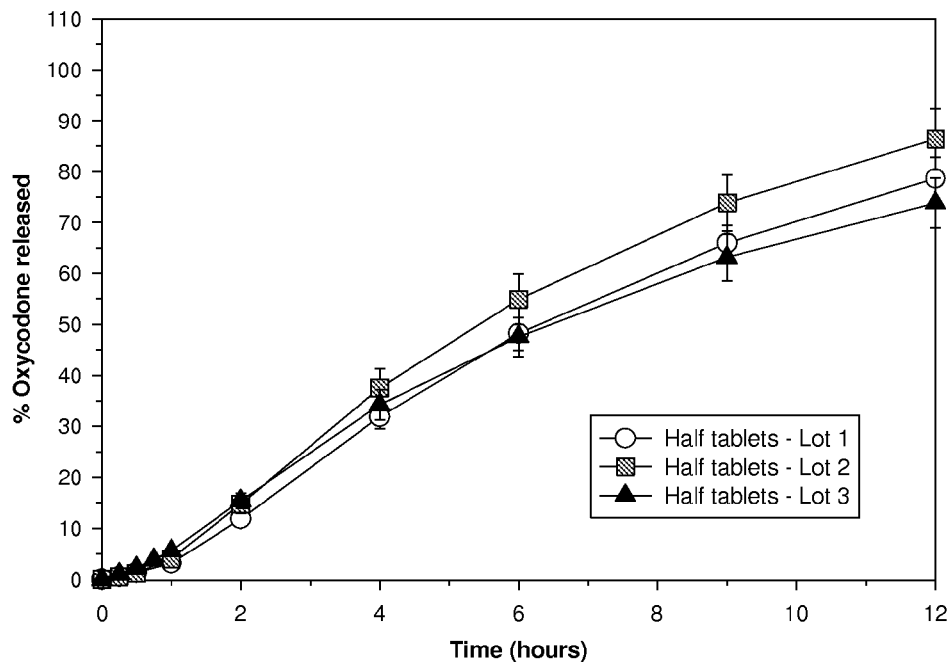
FIGS. 4A and 4B are graphs showing the in vitro dissolution profile of oxycodone HCl from half tablets (FIG. 4A) and quarter tablets (FIG. 4B) of three lots of an exemplary controlled release formulation of the invention in a U.S.P. Type I Apparatus in potassium phosphate buffer at pH 6.8.
Figure 4B:
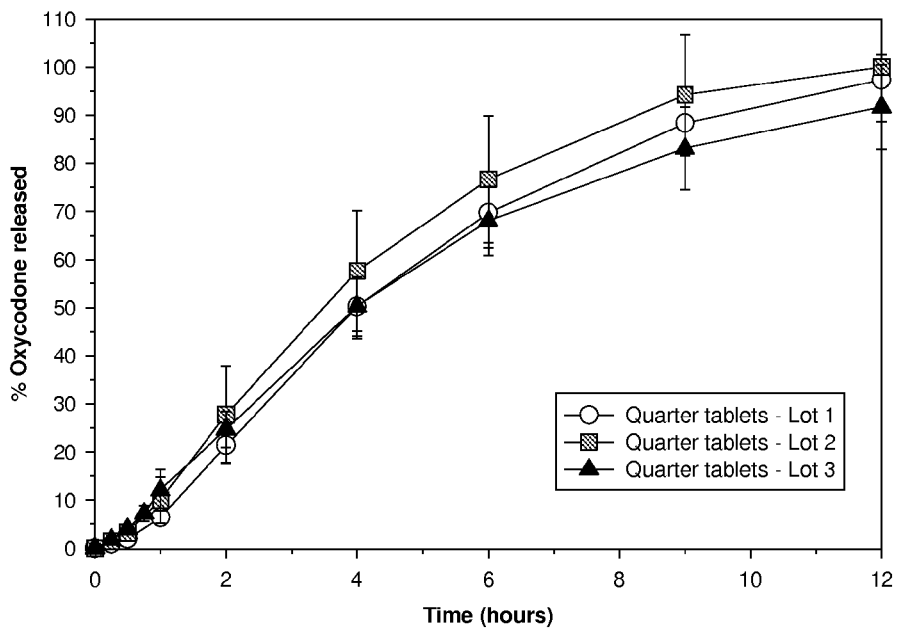
Figure 5A:
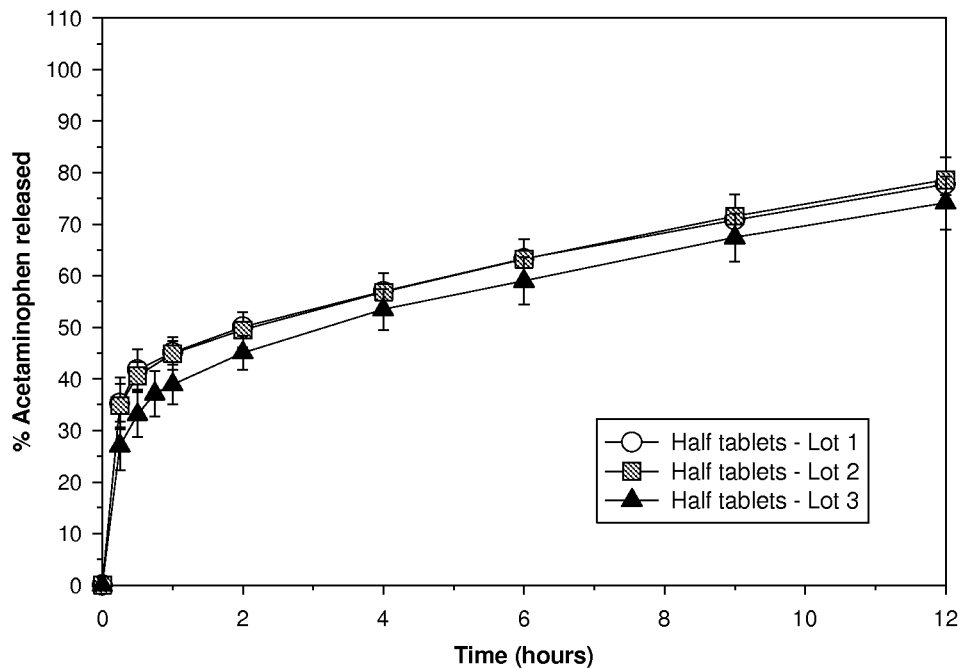
FIGS. 5A and 5B are graphs showing the in vitro dissolution profile of acetaminophen from half tablets (FIG. 5A) and quarter tablets (FIG. 5B) of three lots of an exemplary controlled release formulation of the invention in a U.S.P. Type I Apparatus in potassium phosphate buffer at pH 6.8.
Figure 5B:
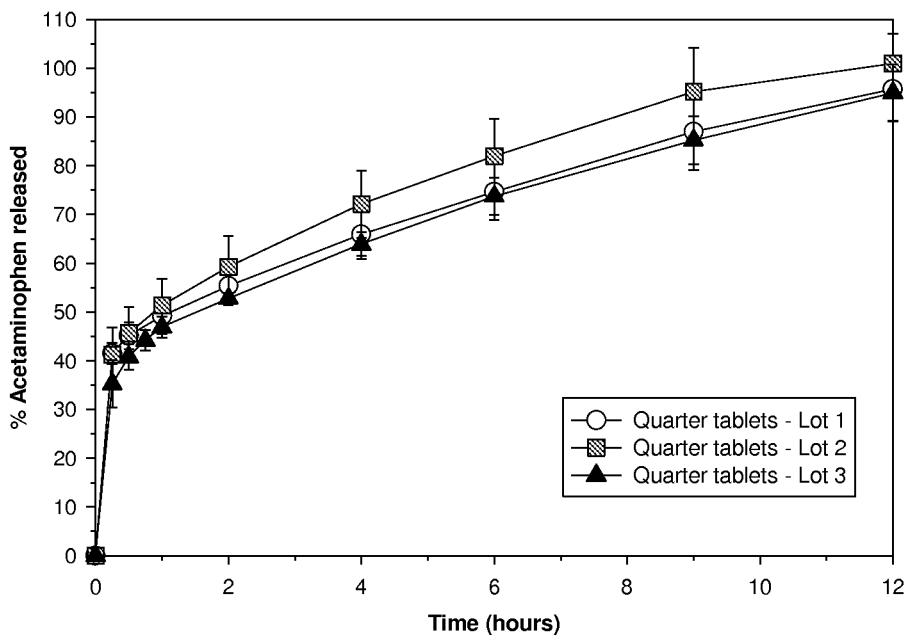

The in vitro release properties of three lots of tablets were measured in a U.S.P. Type I Apparatus in potassium phosphate buffer at pH 6.8. The effect of halving or quartering the tablets on the release of oxycodone is shown in FIGS. 4A (half tablet) and 4B (quarter tablet). The effect of halving or quartering the tablets on the release of acetaminophen is shown in FIGS. 5A (half tablet) and 5B (quarter tablet). The partial tablets maintained a controlled release for 12 hours, with no evidence of dose dumping.

Figure 6A:
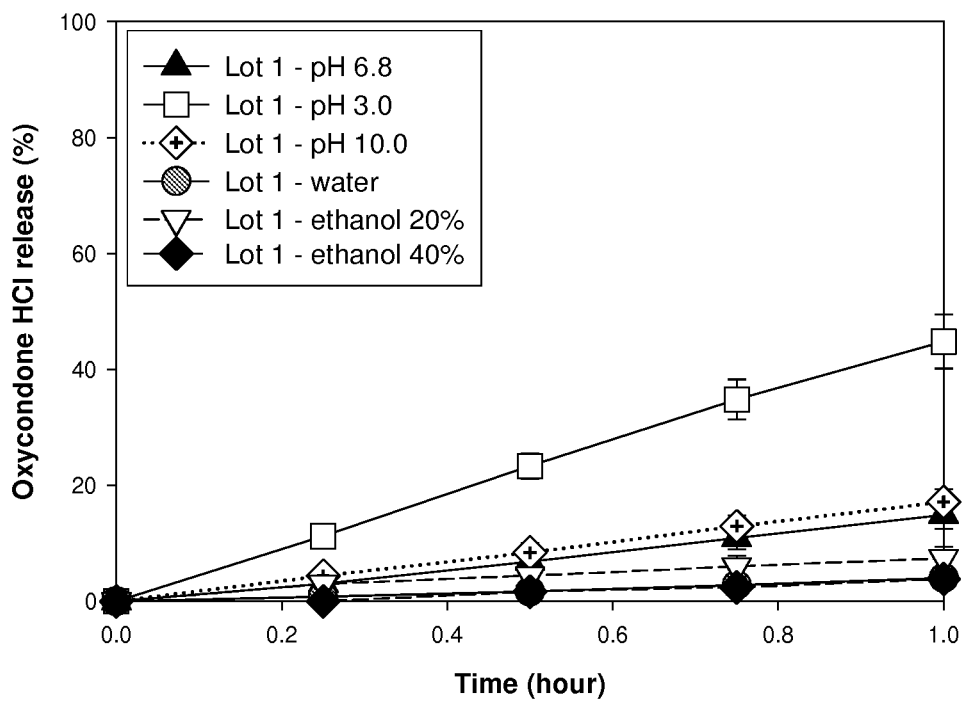
FIGS. 6A and 6B are graphs showing the in vitro dissolution profile of oxycodone HCl (FIG. 6A) and acetaminophen (FIG. 6B) from a crushed, exemplary controlled release formulation of the invention in a U.S.P. Type I Apparatus.
Figure 6B:
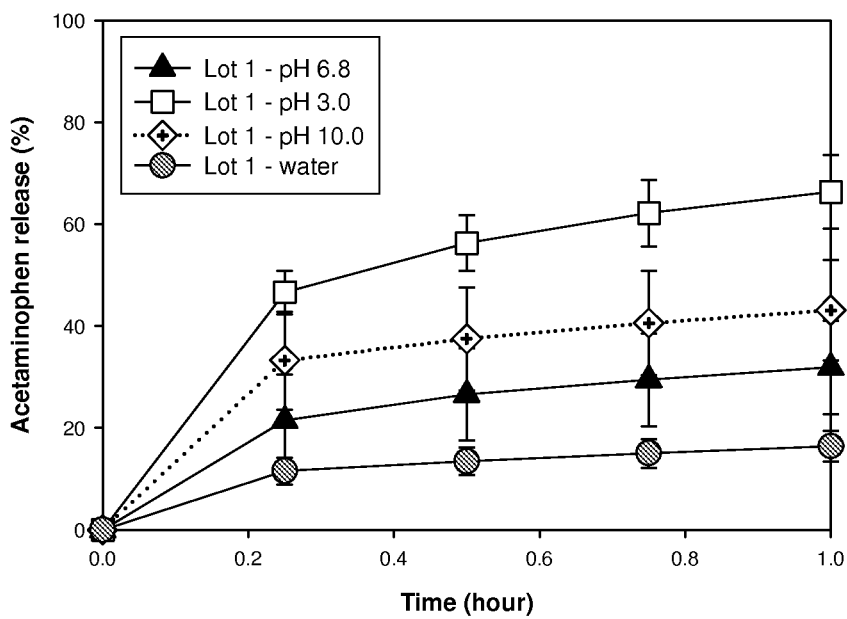

Crushed tablets were prepared using a conventional pill crusher. The in vitro release properties of the crushed tablets were measured in a U.S.P. Type I Apparatus under a variety of conditions. FIG. 6A illustrates the release kinetics of oxycodone in basified potassium phosphate aqueous solution at pH 10.0, potassium phosphate buffer at pH 6.8 and acidified potassium phosphate aqueous solution at pH 3.0, water, water containing 20% ethanol and water containing 40% ethanol. Controlled release of oxycodone was maintained under all conditions with no evidence of dose dumping. FIG. 6B illustrates the release kinetics of acetaminophen, which is less controlled than that of oxycodone. The increased release allows for deterrence of injecting or snorting the crushed powder, which is potentially hepatotoxic. Complete sequestration of acetaminophen after crushing would not allow for such deterrence.

When exposed to water, a crushed tablet rapidly formed a gel, for example, within 21 seconds. Crushed tablets were exposed to the 10 mL of the liquids shown in Table 4. The resulting mixtures were agitated in a mechanical shaker for 120 minutes, then allowed to stand for 15 minutes to determine whether any separation of gel and liquid occurred.

TABLE 4

| Liquid | Oxycodone % released* | Acetaminophen % released* |
|---|---|---|
| Tap Water | Thick gel | Thick gel |
| Ethanol (40% (v/v)) | Thick gel | Thick gel |
| Acidic Media (pH 3.0) | Thick gel | Thick gel |
| Basic Media (pH 10.0) | Thick gel | Thick gel |

As illustrated in Table 4, a thick gel formed when the aqueous solvent contained 40% ethanol or had a pH in the range from 3 to 10. Because the gel did not separate into a solid and supernatant, no liquid was available for analysis to determine the amount of oxycodone or acetaminophen that may have eluted from the composition.*

In order to simulate the effect of intravenous or nasal administration of a crushed tablet, a tablet was crushed and mixed with 2 mL of tap water or water containing 40% ethanol as shown in Table 5. A hard gel formed in both cases. To extract liquid from the hard gel for analysis, a cotton wool filter was placed on the tip of a syringe and a small amount of liquid was extracted under heavy suction. The extracts were analyzed for oxycodone and acetaminophen content.

TABLE 5

| Extract Liquid | % Oxycodone | % Acetaminophen |
| --- | --- | --- |
| Water | 0.0 | 0.14 |
| Ethanol (40% v/v) | 0.0 | 0.12 |

The results show that no oxycodone was detected in the extracts, while a negligible amount of acetaminophen was present in both water and 40% ethanol.

To determine the amount of active ingredient release upon gel disruption, crushed tablets were added to either 100 mL of water, acidified potassium phosphate aqueous solution buffer pH 3.0, or water containing 40% ethanol. The resulting gels were disrupted by vigorous stirring for 1 minute. The mixtures were assayed for oxycodone and acetaminophen content at 15, 30, and 60 seconds as shown in Table 6.

TABLE 6

| | % Oxycodone content | | | % Acetaminophen content | | |
| --- | --- | --- | --- | --- | --- | --- |
| Extract Liquid | 15 sec | 30 sec | 60 sec | 15 sec | 30 sec | 60 sec |
| Water | 0.8 | 1.7 | 2.1 | 30.9 | 42.1 | 49.2 |
| Ethanol (40% v/v) | 2.0 | 2.7 | 4.1 | 29.9 | 44.1 | 52.4 |
| Acidic Media (pH 3.0) | 2.0 | 3.5 | 5.3 | 48.2 | 52.1 | 68.4 |

The results show a rapid release of acetaminophen, which could deter potential intravenous or nasal administration because high doses of acetaminophen are known to be hepatotoxic. Unlike acetaminophen, oxycodone is present as microparticles in the tablet formulation such that release of oxycodone following crushing was minimal.

Example 2

Exemplary Oxycodone HCl/Acetaminophen Tablet

This Example describes the manufacture and testing of a twice-a-day tablet containing oxycodone HCl (20 mg) and acetaminophen (650 mg). The bilayer tablet contains microparticles containing oxycodone HCl and Contramid®, and coated with an enteric coating. The resulting bilayer, however, was encapsulated with a non functional (aesthetic) coat. The superabsorbent material was disposed in the slow release layer.

The formulation of the tablet is set forth in Table 7, and the manufacture of each of the components for the formulation appear in the following sections of this Example.

TABLE 7

| | Tablet Composition | |
| --- | --- | --- |
| Ingredients | (Mg) | (%) |
| First Layer (Slow Release) | | |
| Oxycodone microparticles (coated at 10% Eudragit NE + 15% enteric coating) | 198.4 | 26.40 |
| COMPAP ® (which includes acetaminophen) | 469.44 | 62.46 |
| Carbopol 71 G | 36 | 4.79 |
| Xanthan gum 80 mesh | 36 | 4.79 |
| Colloidal silicon dioxide (Cab O sil) | 2.97 | 0.40 |
| Sodium stearyl fumarate (Pruv) | 8.83 | 1.17 |
| Total | 751.64 | 100 |
| Second layer (Fast Release) | | |
| COMPAP ® (which includes acetaminophen) | 252.77 | 88.42 |
| Microcrystalline Cellulose PH102 | 19.76 | 6.91 |
| Croscarmellose sodium AcDiSol | 6.7 | 2.34 |
| Colloidal silicon dioxide (Cab O sil) | 1.68 | 0.59 |
| Sodium stearyl fumarate (Pruv) | 4.83 | 1.69 |
| FD&C Yellow #6 | 0.13 | 0.05 |
| Total | 285.87 | 100 |

A. Manufacture of Oxycodone Microparticles

The microparticles were produced by mixing the first four components set forth in Table 8. The resulting mixture was subjected to extrusion and spheronization, and the resulting microparticles were coated with the remaining four excipients (Eudragit NE30D, talc, Eudragit L30D-55, triethyl citrate) in a fluid bed coater equipped with a bottom spray. Microparticles coated with a Eudragit L30D-55 coat withstand dissolution at low pH, such as pH 1-3, and prevent the release of oxycodone. The coating dissolves at higher pH, but its mechanical removal is minimal when the tablet is crushed. The coating prevents the release of oxycodone at low pH in both intact and crushed tablets.

The core of the tablet was a bilayer. The oxycodone containing microparticles were incorporated in the slow release layer of the bilayer whereas the acetaminophen, as COMPAP® which was in free form and not incorporated into microparticles, was present in both the rapid release layer and the slow release layer.

TABLE 8

| Ingredients | Mg/tablet | % Composition |
| --- | --- | --- |
| Oxycodone HCl | 20.0 | 10.08 |
| Cellulose microcrystalline (Avicel PH101) | 37.3 | 18.82 |
| Contramid ® | 2.7 | 1.34 |
| Lactose monohydrate | 73.3 | 36.96 |
| Eudragit NE30D | 13.3 | 6.72 |
| Talc | 25.3 | 12.77 |
| Eudragit L30D-55 | 24.0 | 12.1 |
| Triethyl citrate | 2.4 | 1.21 |
| Total | 198.4 | 100.00 |

B. Manufacture of Bilayer

The composition of the first layer (controlled release layer) containing COMPAP® and the oxycodone containing microparticles, and the composition of the second layer containing acetaminophen are shown in Table 7. The bilayer was prepared by mixing the components of each layer and then compressing the materials in a tablet press to form a tablet having a hardness of about 230 N.

C. Aesthetic Coating

The resulting bilayer then was coated with the Opaglos ingredients set forth in Table 9 by using a pan coating machine to form the final coated tablet.

TABLE 9

| Ingredients | Mg/tablet | % tablet |
|---|---|---|
| Opaglos II Green | 31.12 | 3.0 |
| Opaglos II Clear | 10.38 | 1.0 |

Figure 7A:
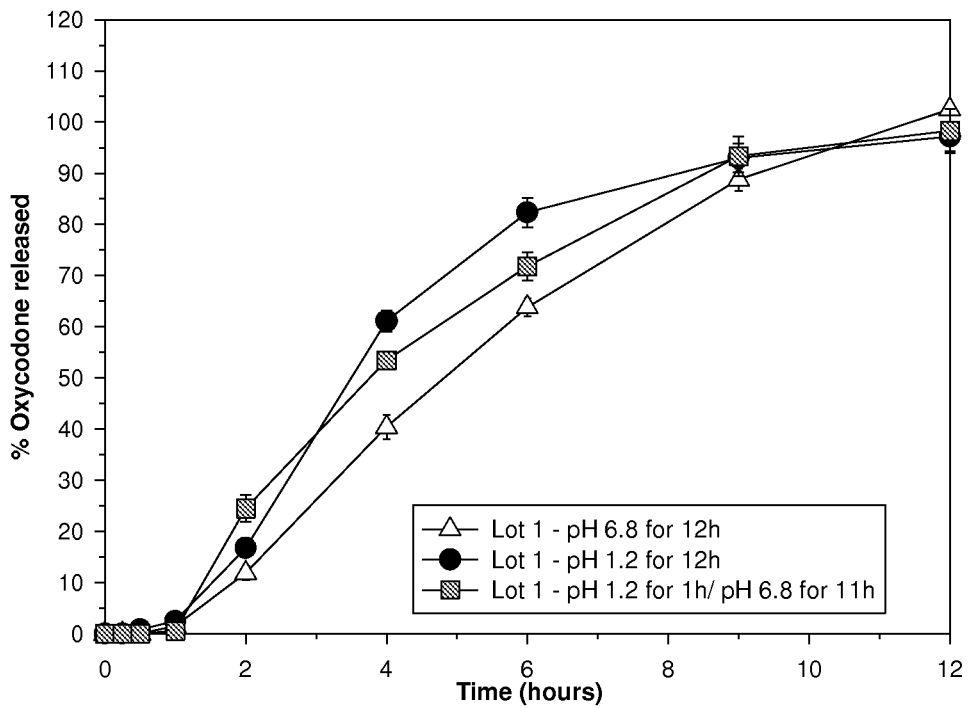
FIGS. 7A and 7B are graphs showing the in vitro dissolution profile of oxycodone HCl (FIG. 7A) and acetaminophen (FIG. 7B) from an intact, exemplary controlled release formulation of the invention in a U.S.P. Type III Apparatus.
Figure 7B:
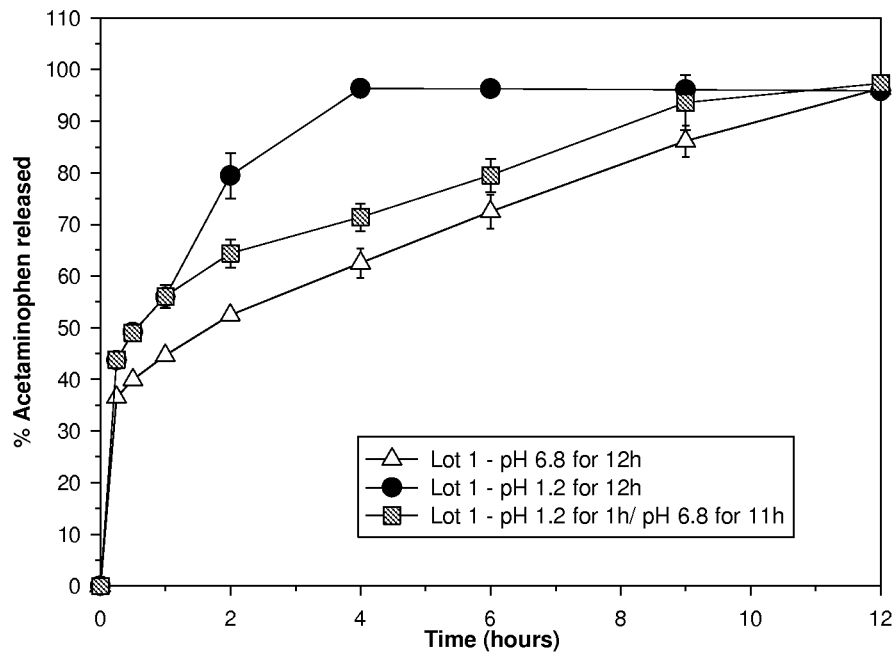

The in vitro release properties of the resulting tablets were measured in a U.S.P. Type I Apparatus in acid pH 1.2 for 12 hours, phosphate buffer pH 6.8 for 12 hours, and acid pH 1.2 for 1 hour, followed by phosphate buffer pH 6.8 for 11 hours. The release kinetics were measured on intact tablets. As shown in FIG. 7A, the release profiles for oxycodone demonstrate the delay in release for at least 1 hour at low pH. As shown in FIG. 7B, a rapid release of acetaminophen was observed. Release kinetics similar to Example 1 were observed for half and quarter tablets (data not shown).

Figure 8A:
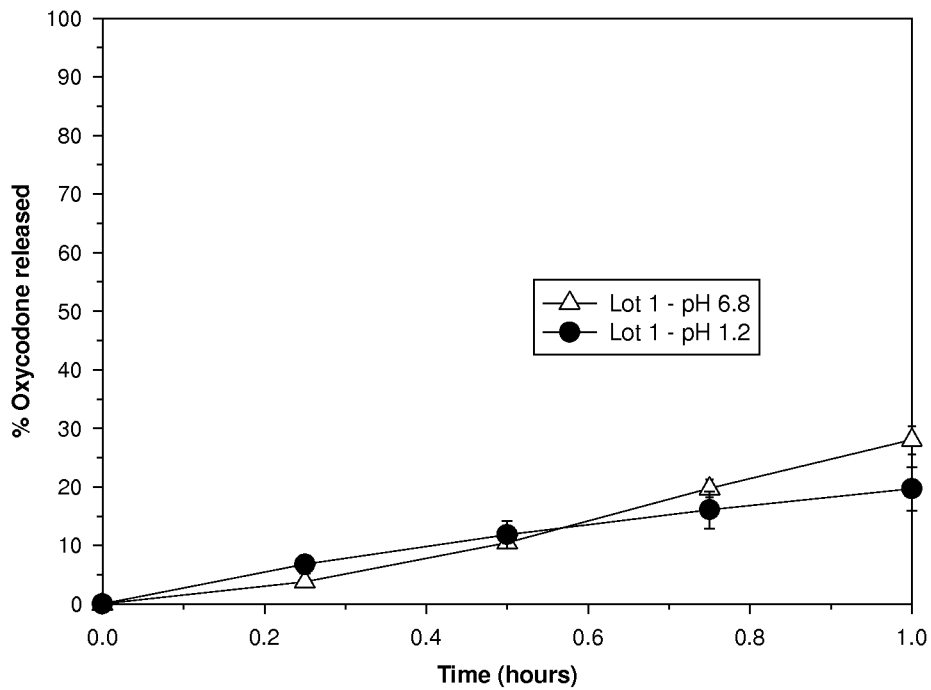
FIGS. 8A and 8B are graphs showing the in vitro dissolution profile of oxycodone HCl (FIG. 8A) and acetaminophen (FIG. 8B) from a crushed, exemplary controlled release formulation of the invention in a U.S.P. Type I Apparatus.
Figure 8B:
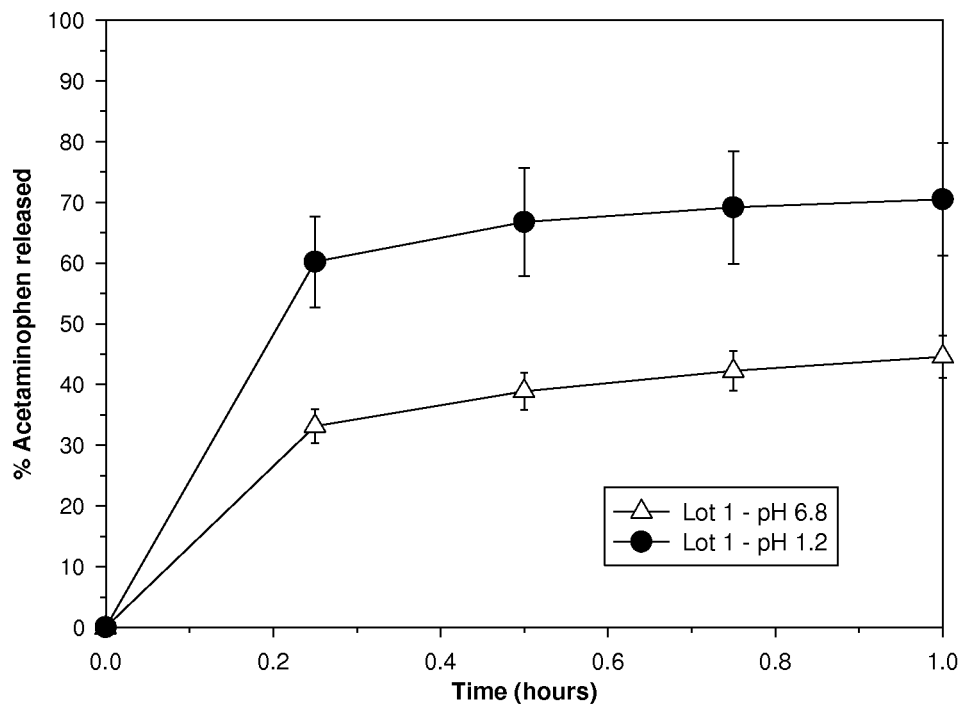

The in vitro release properties of the resulting tablets were measured in a U.S.P. Type I Apparatus in acid pH 1.2 for 1 hour and phosphate buffer pH 6.8 for 1 hour for crushed tablets. As shown in FIG. 8A, the release profiles for oxycodone demonstrate the delay in release for at least 1 hour at low pH. As shown in FIG. 8B, a more rapid release of acetaminophen was observed.

Example 3

Exemplary Oxycodone HCl/Acetaminophen Tablet

This Example describes the manufacture and testing of a tablet (BID) containing oxycodone HCl (20 mg) and acetaminophen (650 mg). The tablet comprises a bilayer core surrounded by an enteric, controlled release coating (namely, Eudragit L30D55). The microparticles, however, did not have a controlled release coating. The superabsorbent material is disposed in the slow release layer.

The microparticles were produced by mixing the components set forth in Table 10 (except for the Eudragit NE 30D and Talc). The resulting mixture was subjected to extrusion and spheronization, and the resulting microparticles were coated with the Eudragit NE 30D and talc in a fluid bed coater equipped with a bottom spray.

TABLE 10

| Ingredients | Mg/tablet | % Composition |
|---|---|---|
| Oxycodone HCl | 20.0 | 11.51 |
| Cellulose microcrystalline (Avicel PH101) | 37.3 | 21.49 |
| Contramid ® | 2.7 | 1.53 |
| Lactose monohydrate | 73.4 | 42.22 |
| Eudragit NE 30D | 20.0 | 11.51 |
| Talc | 20.0 | 11.51 |
| SiO$_2$ | 0.4 | 0.23 |
| Total | 173.8 | 100.00 |

The composition of the core, which was a bilayer, is set forth in Table 11. The oxycodone containing microparticles were incorporated in the slow release layer of the bilayer whereas the acetaminophen, as COMPAP® which was in free form and not incorporated into microparticles, was present in both the rapid release layer and the slow release layer.

TABLE 11

| | Tablet Composition | |
|---|---|---|
| Ingredients | (Mg) | (%) |
| First layer (slow release) | | |
| Oxycodone (provided as oxycodone microparticles) | 173.79 | 24.72 |
| COMPAP ® (which includes acetaminophen) | 433.33 | 61.64 |
| Carbopol 71 G | 42.02 | 5.98 |
| Xanthan gum 80 mesh | 42.02 | 5.98 |
| Colloidal silicon dioxide (Cab O sil) | 2.95 | 0.42 |
| Sodium stearyl fumarate (Pruv) | 8.86 | 1.26 |
| Total | 703.00 | 100.00 |
| Second layer (rapid release) | | |
| COMPAP ® (which includes acetaminophen) | 288.89 | 89.72 |
| Microcrystalline Cellulose PH102 | 19.77 | 6.14 |
| Croscaramellose sodium AcDiSol | 6.70 | 2.08 |
| Colloidal silicon dioxide (Cab O sil) | 1.68 | 0.52 |
| Sodium stearyl fumarate (Pruv) | 4.83 | 1.50 |
| FD&C Yellow #6 | 0.13 | 0.04 |
| Total | 322.00 | 100.00 |

The bilayer core was prepared by mixing the components of each layer and then compressing the materials in a tablet press. The bilayer tablets had a hardness in the range of 190 to 230 Newtons. The resulting bilayer core was then coated with Eudragit L30D 55 by using a pan coating machine. The resulting coating contained 82 mg of Eudragit L30D 55, which accounted for 8% of the weight of the tablet.

Figure 9:
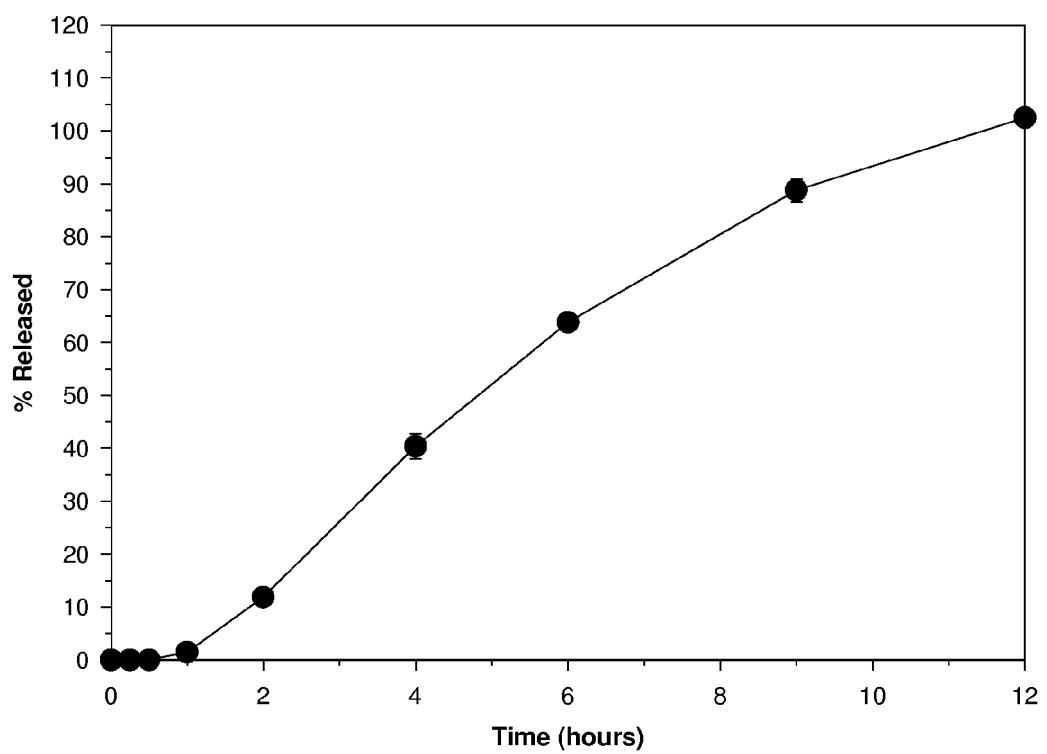
FIG. 9 is a graph showing the in vitro dissolution profile of a coated bilayer embodiment containing 20 mg oxycodone HCl/650 mg acetaminophen, where the release of oxycodone was measured in a U.S.P. Type III Apparatus at 100 rpm for twelve hours in 0.1M hydrochloric acid at pH 1.2 for 1 hour and then in potassium phosphate buffer pH 6.8 for 11 hours.

The in vitro release kinetics of the resulting tablet were measured in a U.S.P. Type III Apparatus at 20 dpm after incubation in 0.1 M hydrochloric acid at pH 1.2 for 1 hour followed by incubation in phosphate buffer pH 6.8 for 11 hours. The results shown in FIG. 9 indicate that no oxycodone was released from the tablet when incubated in 0.1 M hydrochloric acid, but the oxycodone was released in a controlled manner when the buffer was changed to phosphate buffer pH 6.8 after 1 hour.

Example 4

Exemplary Oxycodone HCl/Acetaminophen Tablet

This Example describes the manufacture and testing of a tablet (BID) containing oxycodone HCl (20 mg) and acetaminophen (650 mg). The tablet comprises a bilayer core, where the superabsorbent material (Carbopol 71G) and lipids (Compritol 888 ATO) are present in the controlled release layer. The lipids are designed to swell at low pH thereby minimizing release of oxycodone HCl. The composition of the bilayer core is set forth in Table 12, and the manufacture of each of the components for the formulation appear in the following sections of this Example.

TABLE 12

| | Tablet Composition | |
|---|---|---|
| Ingredients | (Mg) | (%) |
| Rapid Release Layer | | |
| COMPAP ® (which includes acetaminophen) | 288.90 | 89.72 |
| Microcrystalline Cellulose PH102 | 19.76 | 6.14 |
| Croscaramellose sodium AcDiSol | 6.70 | 2.08 |
| Colloidal silicon dioxide (Cab O sil) | 1.68 | 0.52 |
| Sodium stearyl fumarate (Pruv) | 4.83 | 1.50 |

TABLE 12-continued

| Ingredients | Tablet Composition | |
|---|---|---|
| | (Mg) | (%) |
| FD&C Yellow #6 | 0.13 | 0.04 |
| Total | 322.00 | 100.00 |
| Slow Release Layer | | |
| Oxycodone microparticles | 148.58 | 17.38 |
| COMPAP ® (which includes acetaminophen) | 433.42 | 50.70 |
| Carbopol 71 G | 90.00 | 10.53 |
| Compritol 888 ATO | 171.00 | 20.00 |
| Colloidal silicon dioxide (Cab O sil) | 2.96 | 0.35 |
| Sodium stearyl fumarate (Pruv) | 8.83 | 1.03 |
| Total | 854.79 | 100.00 |

A. Manufacture of Oxycodone Microparticles

The microparticles were produced by mixing the components set forth in Table 13 (except for the Eudragit NE 30D and Talc). The resulting mixture was subjected to extrusion and spheronization, and the resulting microparticles were coated with the Eudragit NE 30D and talc in a fluid bed coater equipped with a bottom spray.

TABLE 13

| Ingredients | Mg/batch | Composition |
|---|---|---|
| Oxycodone HCl | 124.8 | 12.48 |
| Cellulose microcrystalline (Avicel PH101) | 232.9 | 23.29 |
| Contramid ® excipient | 16.6 | 1.66 |
| Lactose monohydrate | 457.4 | 45.74 |
| Eudragit NE 30D | 83.2 | 8.32 |
| Talc | 83.2 | 8.32 |
| SiO$_2$ | 2.0 | 0.20 |
| Total | 1000 | 100.00 |

B. Manufacture of Bilayer

The core of the tablet was a bilayer. The oxycodone containing microparticles were incorporated in the slow release layer of the bilayer whereas the acetaminophen, as COMPAP®, which was in free form and not incorporated into microparticles, was present in both the rapid release layer and the slow release layer.

The composition of the first layer (controlled release layer) containing COMPAP® (containing acetaminophen) and the oxycodone containing microparticles, and the composition of the second layer containing COMPAP® are shown in Table 12. The bilayer was prepared by mixing the components of each layer and then compressing the materials in a tablet press (Manesty, UK) to form a tablet having a hardness of about 150 N.

C. Aesthetic Coating

The resulting bilayer was coated with an aesthetic coating using the Opaglos ingredients set forth in Table 14 by using a pan coating machine to provide the final coated tablet.

TABLE 14

| Ingredients | Mg/tablet | % Composition |
|---|---|---|
| Opaglos II Gray | 30.75 | 3.0 |
| Opaglos II Clear | 10.25 | 1.0 |

Figure 10A:
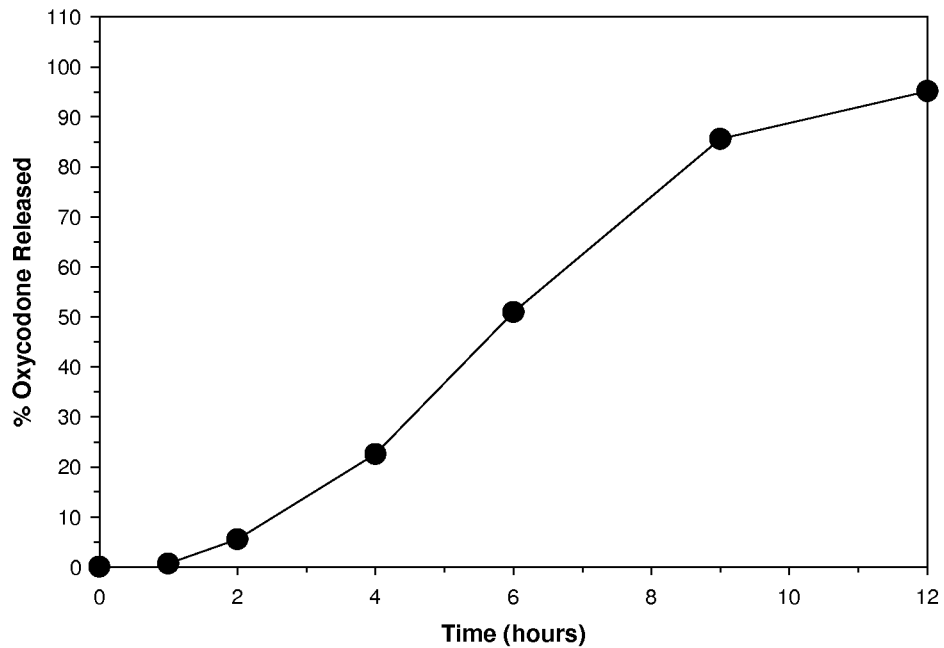
FIGS. 10A and 10B are graphs showing the in vitro dissolution profile of oxycodone HCl (FIG. 10A) and acetaminophen (FIG. 10B) from an intact, exemplary controlled release formulation of the invention in a U.S.P. Type III Apparatus.
Figure 10B:
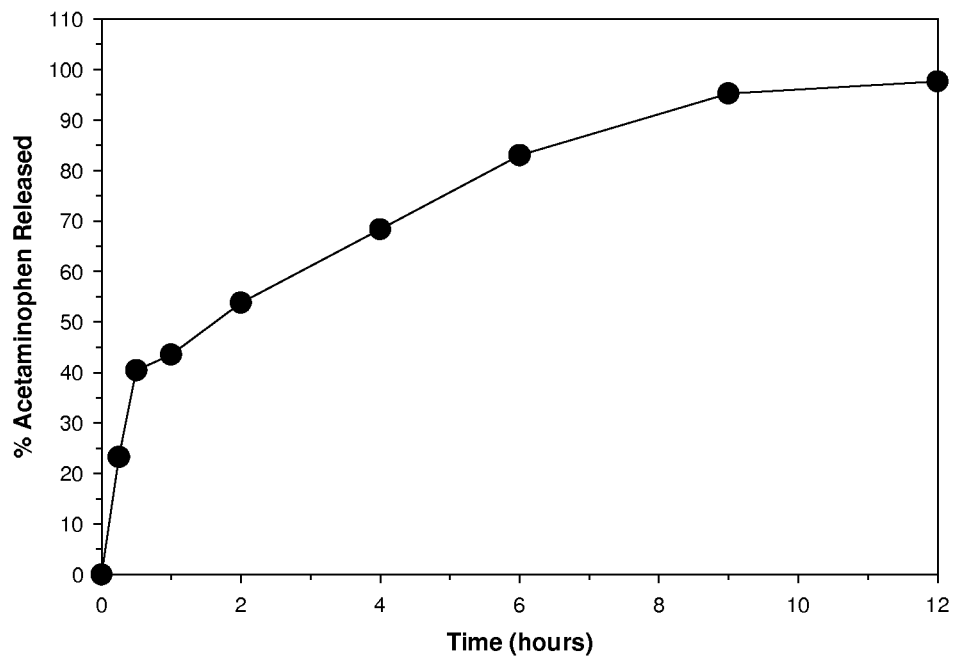

The in vitro release properties of the resulting tablets were measured in a U.S.P. Type III Apparatus in phosphate buffer pH 6.8. The release kinetics were measured on intact tablets. As shown in FIG. 10A, the release profile of oxycodone in tablets comprising Compritol in the controlled release layer was comparable to tablets having an enteric coat on the oxycodone microparticles, such as the data at pH 6.8 for intact tablets in Example 2 under similar conditions (FIG. 7A). Likewise, the release kinetics for acetaminophen shown in FIG. 10B were similar to that of Example 2 (FIG. 7B).

Figure 11A:
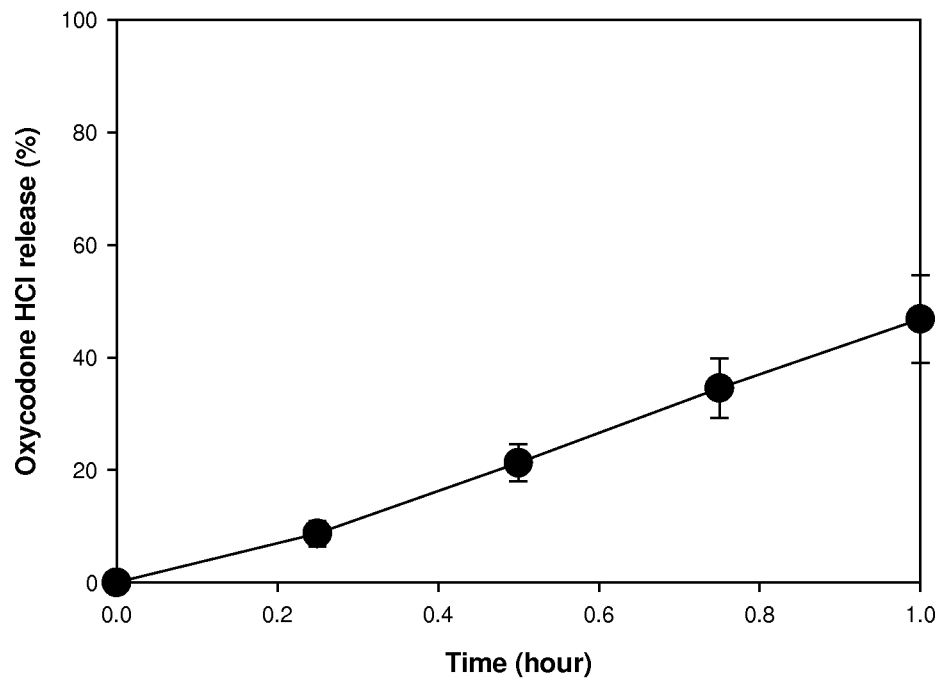
FIGS. 11A and 11B are graphs showing the in vitro dissolution profile of oxycodone HCl (FIG. 11A) and acetaminophen (FIG. 11B) from a crushed, exemplary controlled release formulation of the invention in a U.S.P. Type I Apparatus.
Figure 11B:
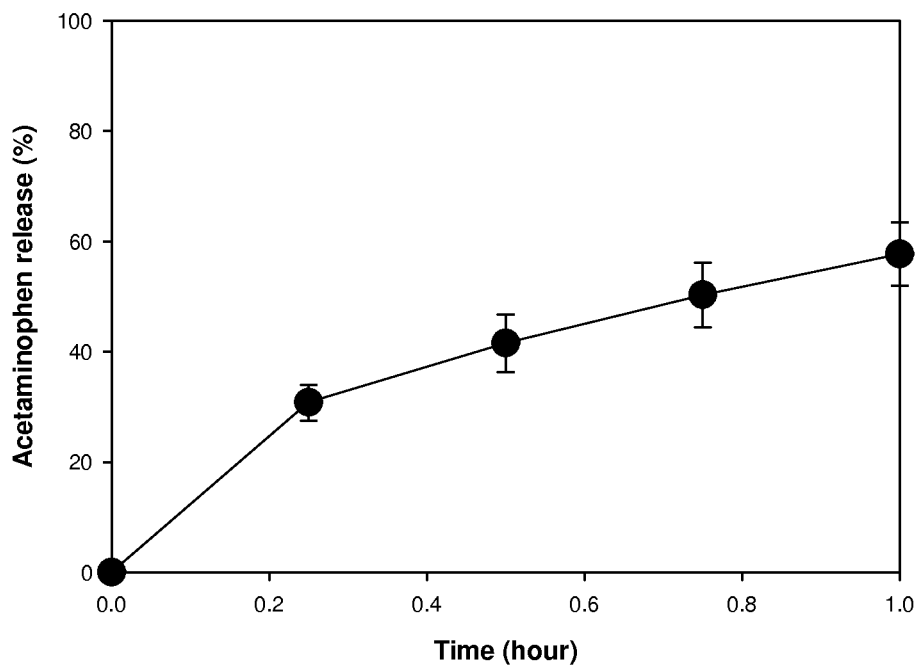

The in vitro release properties of the resulting tablets, when crushed, were measured in a U.S.P. Type I Apparatus in acid at pH 1.2. As shown in FIG. 11A, the release profile of oxycodone in tablets comprising Compritol showed a greater release of oxycodone than the crushed tablets of the Example 2 formulation (FIG. 8A) under the same conditions. However, no dose dumping of oxycodone was observed. In comparison to Example 2 for acetaminophen release from crushed tablets (FIG. 8B), acetaminophen was not released as fast from the Compritol containing crushed tablets (FIG. 11B).

Example 5

Exemplary Controlled Release Methylphenidate Formulation

This Example describes the manufacture and testing of a tablet containing methylphenidate in a 12 hour controlled release bilayer formulation. While the tablet is uncoated, an aesthetic or functional (such as enteric) coat can be applied. The superabsorbent material is disposed within the slow release layer. The formulation of the tablet is set forth in Table 15, and the manufacture of each of the components for the formulation appear in the following sections of this Example.

TABLE 15

| Ingredients | Lot 1 | | Lot 2 | | Lot 3 | | Lot 4 | |
|---|---|---|---|---|---|---|---|---|
| | % | Mg/tab | % | Mg/tab | % | Mg/tab | % | Mg/tab |
| Fast release layer compositions | | | | | | | | |
| Film coated methylphenidate microparticles | 27.31 | 27.31 | 27.31 | 27.31 | 27.31 | 27.31 | 27.31 | 27.31 |
| Avicel PH 102 | 69.17 | 69.17 | 69.17 | 69.17 | 69.17 | 69.17 | 69.17 | 69.17 |
| Croscarmellose (Ac-Di-Sol) | 2.00 | 2.00 | 2.00 | 2.00 | 2.00 | 2.00 | 2.00 | 2.00 |
| Colloidal silicon dioxide | 0.5 | 0.5 | 0.5 | 0.5 | 0.5 | 0.5 | 0.5 | 0.5 |
| Sodium stearyl fumarate | 1.00 | 1.00 | 1.00 | 1.00 | 1.00 | 1.00 | 1.00 | 1.00 |
| Total Core | 100.0 | 100.0 | 100.0 | 100.0 | 100.0 | 100.0 | 100.0 | 100.0 |
| Slow release layer compositions | | | | | | | | |
| Film coated methylphenidate microparticles | 44.22 | 154.8 | 44.22 | 154.8 | 44.22 | 154.8 | 44.22 | 154.8 |

TABLE 15-continued

|  | Lot 1 | | Lot 2 | | Lot 3 | | Lot 4 | |
|---|---|---|---|---|---|---|---|---|
| Ingredients | % | Mg/tab | % | Mg/tab | % | Mg/tab | % | Mg/tab |
| Avicel PH 102 | — | — | — | — | — | — | — | — |
| Carbopol 71G | 13.57 | 47.5 | 13.57 | 47.5 | 13.57 | 47.5 | 20.35 | 71.24 |
| Xanthan gum | 13.57 | 47.5 | 0 | 0 | 0 | 0 | 0 | 0 |
| Kollidon SR | 13.57 | 47.5 | 13.57 | 47.5 | 20.35 | 71.24 | 20.35 | 71.24 |
| Plasdone S-630 | 13.57 | 47.5 | 27.14 | 95.0 | 20.35 | 71.24 | 13.57 | 47.5 |
| Colloidal silicon dioxide | 0.50 | 1.8 | 0.50 | 1.8 | 0.50 | 1.8 | 0.50 | 1.8 |
| Sodium stearyl fumarate | 1.00 | 3.5 | 1.00 | 3.5 | 1.00 | 3.5 | 1.00 | 3.5 |
| Total coat | 100.0 | 350.0 | 100.0 | 350.0 | 100.0 | 350.0 | 100.0 | 350.0 |
| Total tablet weight | | 450.0 | | 450.0 | | 450.0 | | 450.0 |

A. Manufacture of Methylphenidate Microparticles

Microparticles of methylphenidate having the composition set forth in Table 16 were formulated using an extrusion microspheronization process.

TABLE 16

| Ingredients | % Composition |
|---|---|
| Methylphenidate hydrochloride | 29.66 |
| MCC Avicel PH 101 | 55.09 |
| Eudragit RS30D ® + Plasacryl ® + Triethyl citrate | 15.25 |
| Total | 100.00 |

The methylphenidate hydrochloride and MCC Avicel PH 101 were mixed in a mixer for 3 minutes under low shear conditions. The dry blend then was wetted under agitation in the same mixer by gradually adding water until a homogeneous wet mass suitable for extrusion was produced. The wet mass then was extruded at a constant speed (45 rpm) using a Laboratory Multigranulator extruder model MG-55 from LCI, Inc., NC, USA equipped with a dome die having a 0.6 mm diameter hole and a fixed extrusion gap. The extrudates then were spheronized at a constant speed (1800 rpm) using a Marumerzier Model QJ-230T from LCI, Inc., NC, USA. The wet microparticles were dried at 45° C. in a fluid bed (Glatt, GPGC-1) until a moisture content of about 2% was achieved. The resulting microparticles then were coated via fluidized bed coating using a coating solution containing Eudragit RS30D®, a film that resists crushing, but is not an enteric coating.

B. Manufacture of the Bilayer

The composition of the first layer (fast release layer) containing the methylphenidate microparticles (fast release) and the second layer (slow release layer) containing the methylphenidate microparticles (controlled release) are shown in Table 15. The bilayer was prepared by mixing the components of each layer and then compressing the materials using a tablet press to form a tablet having a hardness of about 250 N.

Figure 12:
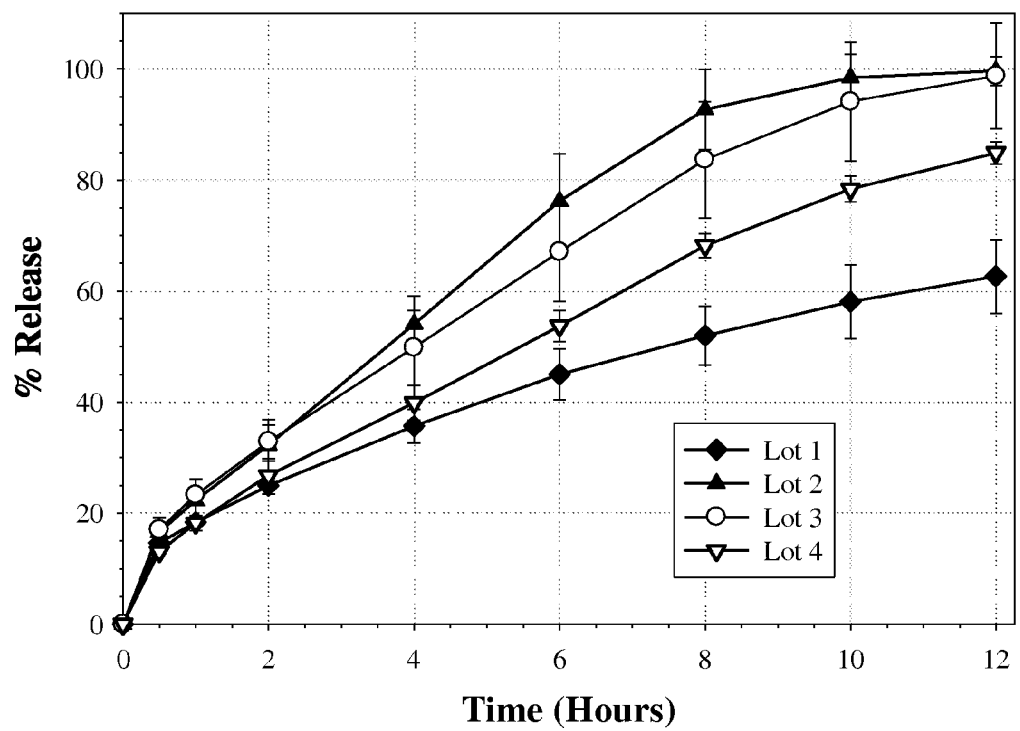
FIG. 12 is a graph showing the in vitro dissolution profile of methylphenidate from four intact, exemplary controlled release formulations of the invention in a U.S.P. Type II Apparatus in acidified water, pH 3.5.

Four lots of tablets were assayed for their in vitro release properties of methylphenidate in a U.S.P. Type II Apparatus in acidified water, pH 3.5. The release kinetics were measured on intact tablets. As shown in FIG. 12, no dose dumping was observed. Approximately 15% methylphenidate was released during the first hour followed by a quasi-zero order release kinetics of methylphenidate up to 12 hours.

Example 6

Exemplary Oxycodone HCl/Acetaminophen Tablets

This Example illustrates the preparation of a bilayer tablet containing oxycodone HCl (20 mg) and acetaminophen (650 mg). One layer is a rapid release layer which contains acetaminophen, and the other layer is a slow release layer which includes oxycodone HCl microparticles and acetaminophen. In this Example, the superabsorbent material is disposed within the rapid release layer.

The formulation of the complete tablet is set forth in Table 17.

TABLE 17

| Ingredients | Mg/Tablet | %/Tablet |
|---|---|---|
| Oxycodone HCl (as Oxycodone HCl microparticles - theoretical content = 9.29%) | 20.0 | 1.76 |
| COMPAP ® (which includes acetaminophen) | 722.22 | 63.69 |
| Microcrystalline cellulose PH101 | 37.32 | 3.29 |
| Contramid ® bulk powder | 2.67 | 0.24 |
| Lactose monohydrate (Spray Dry) #315 | 73.31 | 6.46 |
| Eudragit NE30D | 19.99 | 1.76 |
| Talc Suprafino H | 32.99 | 2.91 |
| Eudragit L30D-55 | 25.99 | 2.29 |
| Triethyl citrate | 2.60 | 0.23 |
| Mannitol | 34.79 | 3.07 |
| Microcrystalline Cellulose PH102 | 21.80 | 1.92 |
| Croscarmellose sodium AcDiSol | 6.70 | 0.59 |
| Carbomer homopolymer Type A carbomer 941 (granular) | 34.79 | 3.07 |
| FD&C Yellow #6 Aluminium Lake (35-42) | 0.13 | 0.01 |
| Xanthan gum 80 mesh | 80.00 | 7.05 |
| Colloidal Silicon Dioxide | 5.08 | 0.45 |
| Sodium stearyl fumarate | 13.66 | 1.20 |
| Total | 1134.03 | 100% |

A. Manufacture of the Rapid Release Layer

COMPAP® and the ingredients of the rapid release layer given in Table 18 were blended in a V-blender and set aside for a later stage of the tablet preparation.

TABLE 18

| | Tablet Composition | |
|---|---|---|
| Ingredients | (Mg) | (%) |
| COMPAP ® (which includes acetaminophen) | 252.78 | 75.30 |
| Mannitol | 34.79 | 10.36 |
| Carbopol 71 G | 34.79 | 10.36 |
| Croscarmellose sodium AcDiSol | 6.70 | 2.00 |
| Colloidal silicon dioxide (Cab O sil) | 1.68 | 0.5 |
| Sodium stearyl fumarate (Pruv) | 4.83 | 1.44 |
| FD&C Yellow #6 Aluminum Lake (35-42) | 0.13 | 0.04 |
| Total | 335.70 | 100.00 |

B. Manufacture of Oxycodone HCl Microparticles

A wet mass of the first four ingredients (including oxycodone HCl) given in Table 19 was extruded, spheronized, dried, and sieved to give uncoated microparticles. The microparticles then were coated with a polymer solution of Eudragit NE30D and talc, followed by coating with a polymer solution of Eudragit L30D-55, triethyl citrate, and talc. The coated microparticles were then mixed with colloidal silicon dioxide and cured in an oven for 18 hours at 40° C.

TABLE 19

| Ingredients | Microsphere Composition (%) |
|---|---|
| Oxycodone HCl | 9.29 |
| Cellulose microcrystalline (Avicel PH101) | 17.34 |
| Contramid ® | 1.24 |
| Lactose monohydrate | 34.05 |
| Eudragit NE30D | 9.29 |
| Talc | 15.32 |
| Eudragit L30D-55 | 12.07 |
| Triethyl citrate | 1.21 |
| Colloidal silicon dioxide | 0.20 |
| Total | 100% |

C. Manufacture of the Slow Release Layer

The oxycodone HCl microparticles and the ingredients of the slow release layer given in Table 20 were blended in a V-blender.

TABLE 20

| | Tablet Composotion | |
|---|---|---|
| Ingredients | (Mg) | (%) |
| Oxycodone HCl microparticles (9.29% theoretical) | 215.29 | 26.97 |
| COMPAP ® (which includes acetaminophen) | 469.44 | 58.80 |
| Xanthan gum 80 mesh | 80.00 | 10.02 |
| Microcrystalline cellulose PH102 | 21.80 | 2.73 |
| Colloidal silicon dioxide (Cab O sil) | 2.97 | 0.37 |
| Sodium stearyl fumarate (Pruv) | 8.83 | 1.11 |
| Total | 798.33 | 100.00 |

D. Manufacture of the Tablet

The blended rapid release layer and the blended slow release layer were compressed on a rotary bilayer Picolla 11-station press to provide caplet shaped tablets. The characteristics of the tablets obtained are summarized in Table 21.

TABLE 21

| Tablet Characteristics | Typical Value |
|---|---|
| Weight (mg) | 1134 |
| Shape | Caplet |
| Length × width × thickness (mm) | 18.5 × 9.3 × 7.6 |
| Hardness (N) | 180 |

Figure 13A:
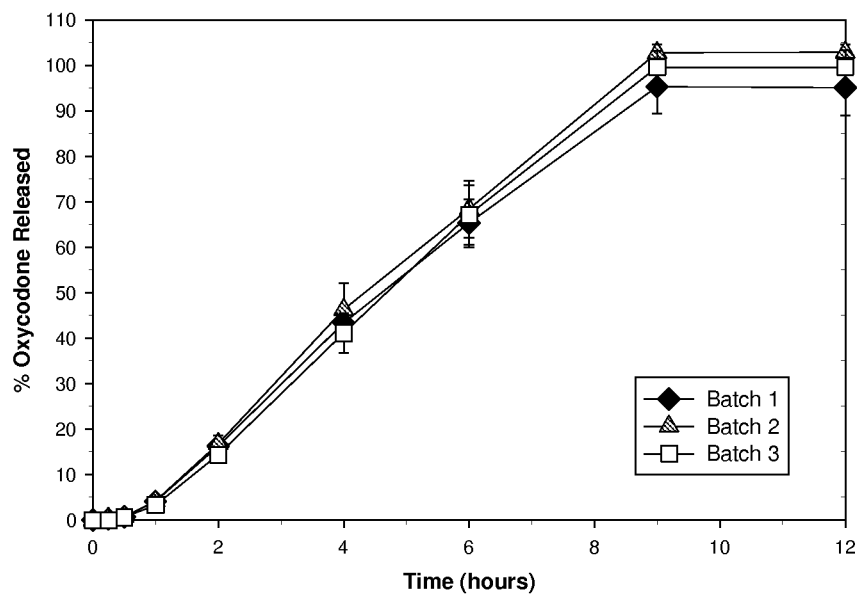
FIGS. 13A and 13B are graphs showing the in vitro dissolution profile of oxycodone HCl (FIG. 13A) and acetaminophen (FIG. 13B) from three intact exemplary controlled release formulations of the invention in a U.S.P. Type III Apparatus in phosphate buffer, pH 6.8.
Figure 13B:
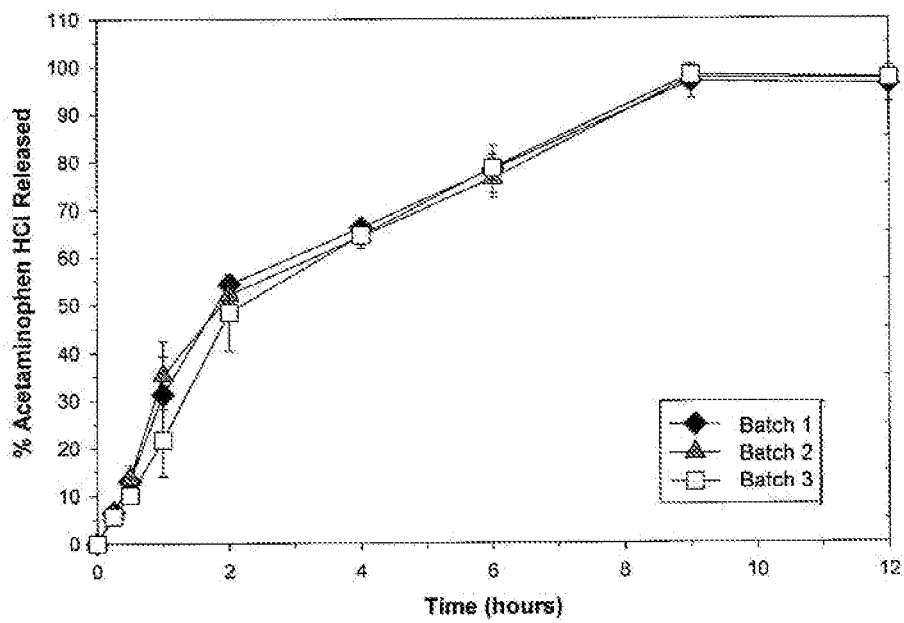

The in vitro release kinetics of the resulting uncoated tablet were measured in a U.S.P. Type III Apparatus at 20 dpm in 250 mL of phosphate buffer, pH 6.8. The release kinetics were measured on three batches of intact tablets for 12 hours. As shown in FIGS. 13A and 13B, the release profiles for oxycodone HCl and acetaminophen, respectively, were substantially the same across the three samples.

Figure 14A:
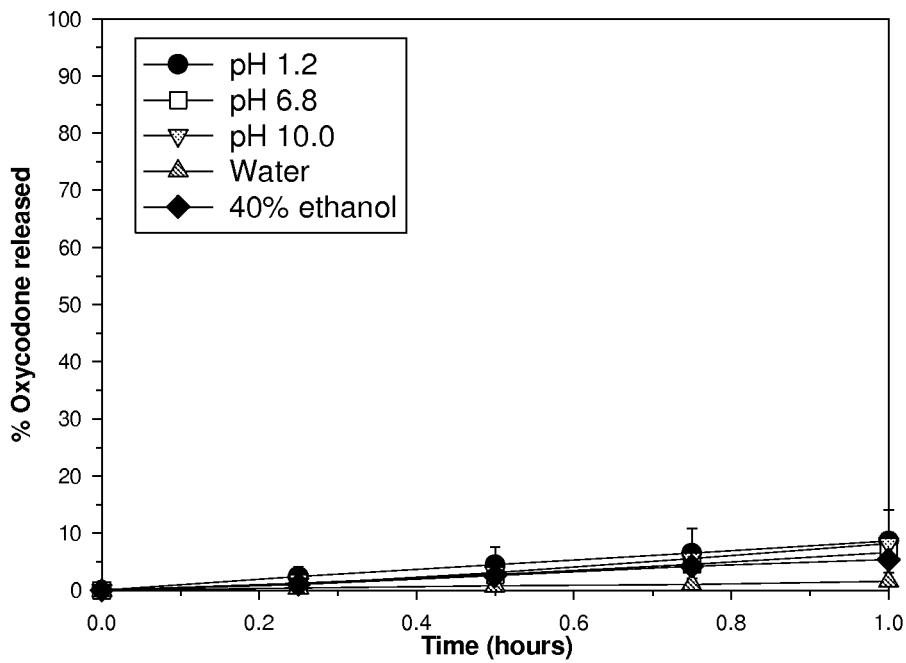
FIGS. 14A and 14B are graphs showing the in vitro dissolution profiles of oxycodone HCl (FIG. 14A) and acetaminophen (FIG. 14B) from uncoated crushed exemplary controlled release formulations of the invention as measured in a U.S.P. Type I Apparatus in potassium phosphate buffer pH 1.2 (-●-), pH 6.8 (-□-), and pH 10 (-▼-), in water (-▲-), and in 40% ethanol (-◆-).
Figure 14B:
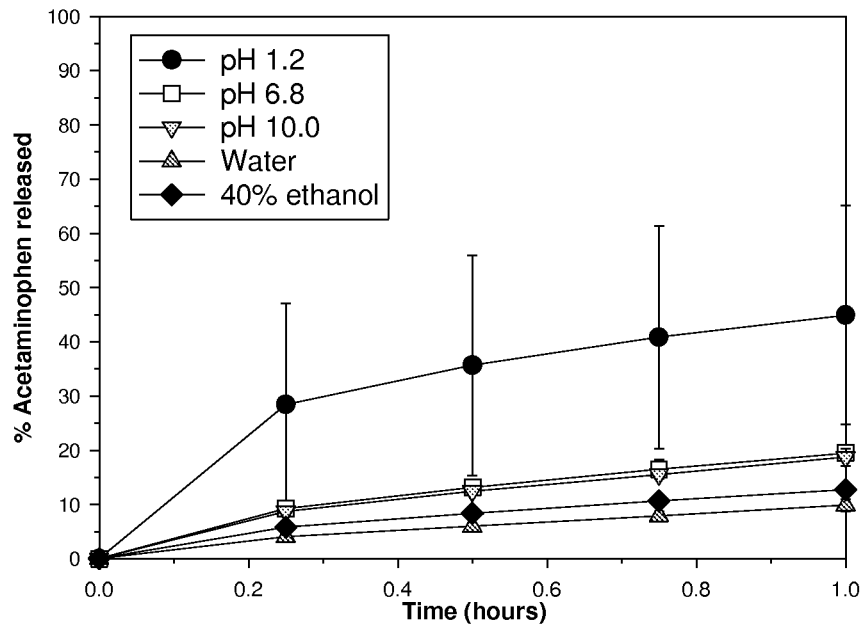

The in vitro release kinetics of oxycodone HCl from uncoated crushed tablets were measured in a U.S.P. Type I Apparatus in potassium phosphate aqueous solutions at pH 1.2, 6.8, and 10, in water, and in 40% ethanol as shown in FIG. 14A. Less than 10% of the oxycodone HCl was released in the various media. The in vitro release kinetics of acetaminophen from uncoated crushed tablets were measured in a U.S.P. Type I Apparatus, in potassium phosphate aqueous solutions at pH 1.2, 6.8, and 10, in water, and in 40% ethanol as shown in FIG. 14B. Less than 50% of the acetaminophen was released in one hour in aqueous solution at pH 1.2, and less than 20% of the acetaminophen was released at one hour in the other media.

Figure 15A:
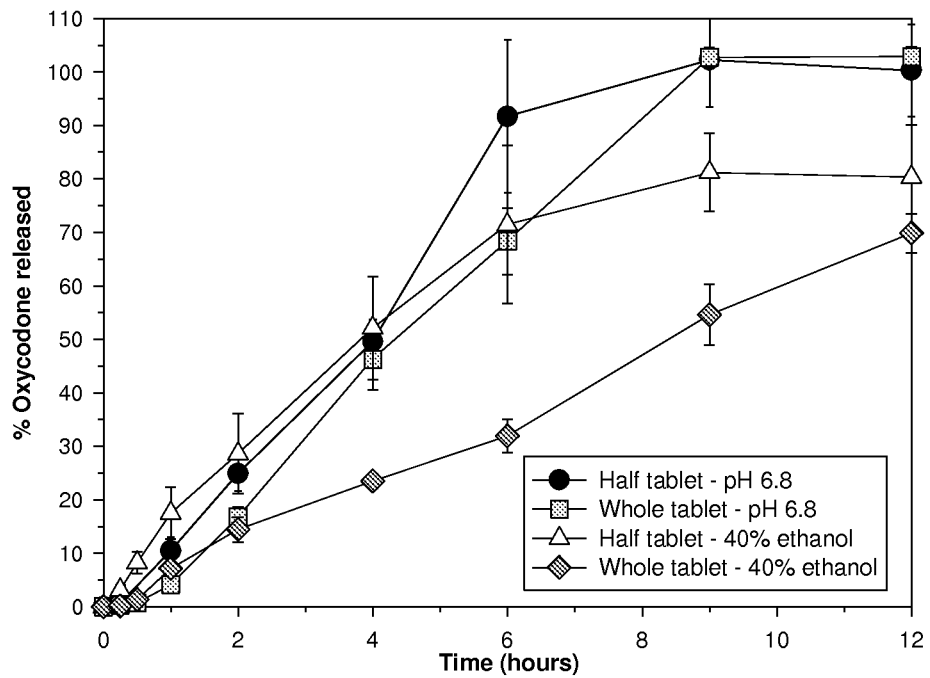
FIGS. 15A and 15B are graphs showing the in vitro dissolution profiles of oxycodone HCl (FIG. 15A) and acetaminophen (FIG. 15B) from whole and bisected exemplary controlled release formulations of the invention as measured in a U.S.P. Type III Apparatus.
Figure 15B:
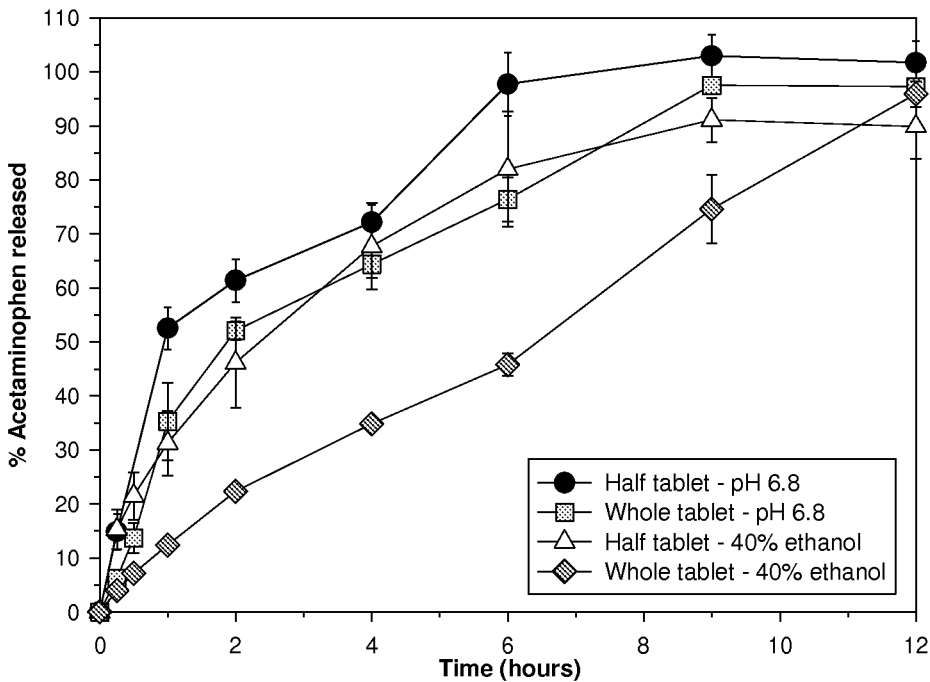

The in vitro release kinetics of oxycodone HCl and acetaminophen from whole and bisected (half) tablets were measured in a U.S.P. Type III Apparatus, 20 dpm, in 250 mL of potassium phosphate buffer, pH 6.8. The in vitro release kinetics of oxycodone HCl and acetaminophen from bisected (half) tablets were also measured in a U.S.P. Type III Apparatus in 40% ethanol. The effect of bisecting the tablets on the release of oxycodone is shown in FIG. 15A, which depicts release profiles for whole and half tablets. The effect of bisecting the tablets on the release of acetaminophen is shown in FIG. 15B, which depicts release profiles for whole and half tablets. The half tablet and the full tablet in general displayed similar release characteristics. The release of oxycodone and acetaminophen was slower in 40% ethanol from whole tablets than from bisected tablets.

The misuse prevention properties of the crushed uncoated tablets were determined by simple extraction into tap water, 40% ethanol, and potassium phosphate aqueous solutions at pH 1.2, 6.8, and 10. The results are given in Table 22. Oxycodone release was well controlled in all media, while an increase in acetaminophen release was observed at buffer pH 1.2 and 6.8.

TABLE 22

| | Oxycodone HCl | | | Acetaminophen | | |
|---|---|---|---|---|---|---|
| Tests | 15 sec (%) | 30 sec (%) | 60 sec (%) | 15 sec (%) | 30 sec (%) | 60 sec (%) |
| Tap Water | 0.4 | 0.7 | 0.8 | 22.1 | 33.1 | 24.4 |
| Ethanol (40%) | 1.6 | 1.6 | 1.7 | 17.6 | 15.5 | 13.3 |
| Buffer pH 1.2 | 1.4 | 2.3 | 1.3 | 32.4 | 45.3 | 43.8 |
| Buffer pH 6.8 | 2.2 | 6.2 | 2.1 | 33.3 | 48.4 | 40.8 |
| Buffer pH 10.0 | 0.5 | 0.7 | 0.6 | 21.2 | 26.4 | 28.0 |

Example 7

Exemplary Oxycodone HCl/Acetaminophen Tablets

This Example illustrates the preparation of a bilayer tablet containing oxycodone HCl (20 mg) and acetaminophen (650 mg). One layer is a rapid release layer which contains acetaminophen, and the other layer is a slow release layer which contains oxycodone HCl microparticles and acetaminophen. The superabsorbent material is disposed within the slow release layer. The formulation of the tablet is set forth in Table 23.

TABLE 23

| | Tablet Composition | |
|---|---|---|
| Ingredients | (Mg) | (%) |
| Second Layer (Rapid Release) | | |
| COMPAP ® (which includes acetaminophen) | 252.8 | 88.4 |
| Microcrystalline Cellulose PH 102 | 19.8 | 6.9 |
| Sodium Croscarmellose | 6.7 | 2.4 |
| Colloidal Silicon Dioxide | 1.7 | 0.6 |

TABLE 23-continued

| Ingredients | Tablet Composition | |
|---|---|---|
| | (Mg) | (%) |
| Sodium stearyl fumarate (Pruv ®) | 4.8 | 1.7 |
| FD&C Yellow #6 Aluminum Lake (35-42) | 0.1 | 0.05 |
| Total | 285.9 | 100.0 |
| First Layer (Slow Release) | | |
| Oxycodone microparticles | 214.8 | 25.8 |
| COMPAP ® (which includes acetaminophen) | 469.4 | 56.4 |
| Microcrystalline Cellulose PH 102 | 20.0 | 2.4 |
| Carbopol ® 71 G | 38.5 | 4.6 |
| Kollidon SR | 57.8 | 7.0 |
| HPMC K100M | 19.3 | 2.3 |
| Colloidal Silicon Dioxide | 3.0 | 0.4 |
| Sodium stearyl fumarate (Pruv ®) | 8.8 | 1.1 |
| Total | 831.7 | 100.0 |

A. Manufacture of the Rapid Release Layer

COMPAP® and the ingredients of the rapid release layer given in Table 23 were blended in a V-blender and set aside for a later stage of the tablet preparation.

B. Manufacture of the Slow Release Layer

Oxycodone HCl microparticles were prepared according to the procedure of Example 6. The microparticles and the ingredients of the slow release layer given in Table 23 were blended in a V-blender.

C. Manufacture of the Tablet

The blended rapid release layer and the blended slow release layer were compressed on a rotary bilayer Picolla 11-station press to provide caplet shaped tablets. The characteristics of the tablets obtained are summarized in Table 24.

TABLE 24

| Tablet Characteristics | Typical Value |
|---|---|
| Weight (mg) | 1117.6 |
| Shape | Caplet |
| Length × width × thickness (mm) | 18.5 × 9.3 × 7.2 |
| Hardness (N) | 250 |

Figure 16:
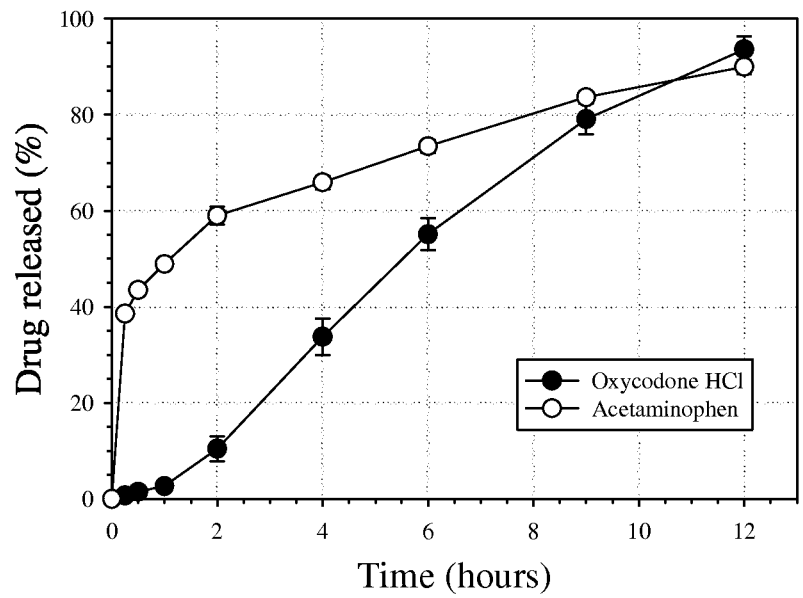
FIG. 16 is a graph showing the in vitro dissolution profiles of oxycodone HCl (-●-) and acetaminophen (-○-) from intact exemplary controlled release formulations of the invention as measured in a U.S.P. Type III Apparatus for 1 hour in acid medium, pH 1.2, followed by 11 hours in phosphate buffer, pH 6.8.

The in vitro release kinetics of oxycodone HCl and acetaminophen for the resulting intact bilayer tablets were measured in a U.S.P. Type III Apparatus for 1 hour in acid medium, pH 1.2, followed by 11 hours in phosphate buffer, pH 6.8. The results are summarized in FIG. 16, which show that drug release for acetaminophen is faster than the release of oxycodone.

Figure 17:
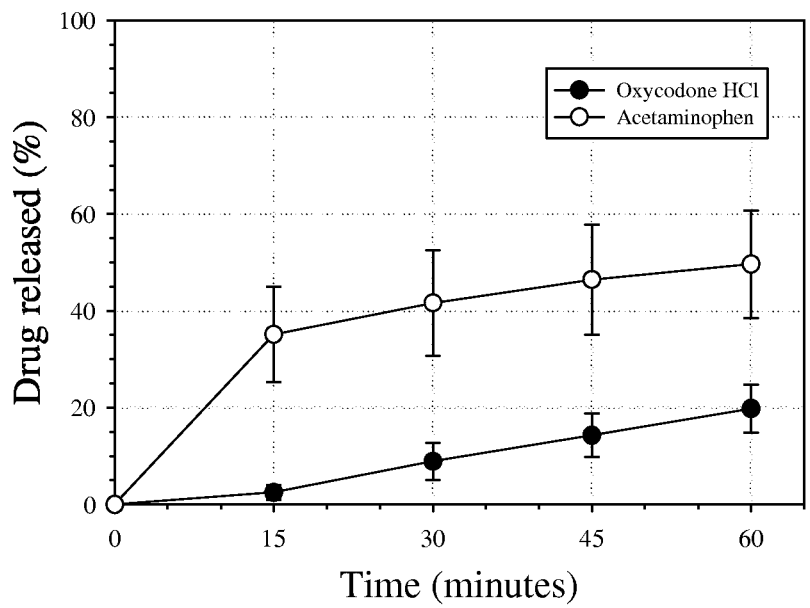
FIG. 17 is a graph showing the in vitro dissolution profiles of oxycodone HCl (-●-) and acetaminophen (-○-) from crushed exemplary controlled release formulations of the invention as measured in a U.S.P. Type I Apparatus in deionized water.

The in vitro release kinetics of oxycodone HCl and acetaminophen for the resulting crushed bilayer tablets were measured in a U.S.P. Type I Apparatus in 900 mL of deionized water at 100 rpm for 60 hours. The results are summarized in FIG. 17, which show that the drug release for oxycodone is much slower than the release of acetaminophen.

INCORPORATION BY REFERENCE

The entire disclosure of each of the patent and scientific documents referred to herein is incorporated by reference for all purposes.

EQUIVALENTS

Although the present invention has been illustrated by means of preferred embodiments thereof, it is understood that the invention intends to cover broad aspects thereof without departing from the spirit and scope of the invention as defined in the appended claims.

What is claimed is:

1. A solid, compressed controlled release composition for oral administration of at least one pharmaceutically active agent, comprising:
   (a) a first layer comprising a first population of controlled release microparticles having a pharmaceutically active agent disposed therein;
   (b) a second layer adjacent the first layer and comprising a superabsorbent material comprising a cross-linked acrylic acid polymer characterized in that the cross-linked acrylic acid polymer absorbs at least 15 times its own weight of water, the second layer comprising from about 10% to about 50% w/w of the superabsorbent material;
   (c) a controlled release agent disposed within the first layer, the second layer, or both the first layer and the second layer; and
   (d) the composition having a hardness from about 200 N to about 400 N, and wherein the composition,
      (i) when intact and exposed to an aqueous medium, the pharmaceutically active agent is released from the formulation over a prolonged period of time,
      (ii) when crushed and exposed to 2 mL of water, the superabsorbent material absorbs all of the water and creates a hard gel that traps the microparticles, whereupon the hard gel and the microparticles provide controlled release of the pharmaceutically active agent disposed within the microparticles, and
      (iii) when broken and exposed to 900 mL of water in a U.S.P. Type I Apparatus with stirring at 100 rpm for 30 minutes at 37° C., less than about 50% by weight of the pharmaceutically active agent originally present in the formulation before it was broken is released into the water.

2. The composition of claim 1, wherein the first layer further comprises a superabsorbent material comprising a cross-linked acrylic acid polymer characterized in that the cross-linked acrylic acid polymer absorbs at least 15 times its own weight of water.

3. The composition of claim 1, wherein the pharmaceutically active agent present in the first layer is released over a period of at least 6 hours.

4. The composition of claim 3, wherein the pharmaceutically active agent present in the first layer is released over a period of at least 12 hours.

5. The composition of claim 1, wherein the composition further comprises a coating that encapsulates the first layer and the second layer.

6. The composition of claim 5, wherein the coating is a controlled release coating.

7. The composition of claim 1, wherein the controlled release microparticles are coated with a controlled release film.

8. The composition of claim 1, wherein the microparticles have an average diameter in the range of from about 1 μm to about 1000 μm or in the range of from about 300 μm to about 800 μm.

9. The composition of claim 8, wherein the microparticles have an average diameter of about 700 μm.

10. The composition of claim 8, wherein the microparticles have an average diameter in the range of from about 1 μm to about 400 μm or in the range of from about 10 μm to about 200 μm.

11. The composition of claim 10, wherein the microparticles have an average diameter of about 100 μm.

12. The composition of claim 1, wherein, in element (iii), less than about 25% by weight of the pharmaceutically active agent originally present in the composition before it was broken is released into the water.

13. The composition of claim 1, wherein, when the composition is broken and exposed to 900 mL of an aqueous solution containing 60% (v/v) ethanol in a U.S.P. Type 1 Apparatus with stirring at 100 rpm for 30 minutes at 37° C., less than about 50% by weight of a pharmaceutically active agent originally present in the composition before it was broken is released into the aqueous solution.

14. The composition of claim 13, wherein less than about 25% by weight of the pharmaceutically active agent originally present in the composition before it was broken is released into the aqueous solution.

15. The composition of claim 1, wherein the composition is in the form of a capsule, caplet, pill, or a compressed tablet.

16. The composition of claim 1, wherein the pharmaceutically active agent is a drug capable of abuse.

17. The composition of claim 16, wherein the drug is an opioid analgesic, hypnotic agent, an anxiolytic or a respiratory stimulant.

18. The composition of claim 1, wherein the cross-linked acrylic acid polymer is a copolymer.

19. The composition of claim 1, wherein the cross-linked acrylic acid polymer is selected from the group consisting of an acrylic acid polymer cross-linked with divinyl glycol, an acrylic acid polymer cross-linked with allyl ethers of pentaerythritol, and a mixture thereof.

20. The composition of claim 1, wherein the cross-linked acrylic acid polymer is polycarbophil.

21. The composition of claim 1, wherein the cross-linked acrylic acid polymer is polycarbophilic calcium.

22. The composition of claim 1, wherein the cross-linked acrylic acid polymer is a carbomer homopolymer type A.

23. The composition of claim 1, wherein the cross-linked acrylic acid polymer is a carbomer homopolymer type B.

24. A method of providing controlled release of a pharmaceutically active agent, the method comprising orally administering to an individual in need of the pharmaceutically active agent the composition of claim 1.

* * * * *